United States Patent
Burckhardt

(10) Patent No.: US 9,290,603 B2
(45) Date of Patent: *Mar. 22, 2016

(54) AMINES HAVING SECONDARY ALIPHATIC AMINO GROUPS

(75) Inventor: Urs Burckhardt, Zurich (CH)

(73) Assignee: SIKA TECHNOLOGY AG, Baar (CH)

(*) Notice: Subject to any disclaimer, the term of this patent is extended or adjusted under 35 U.S.C. 154(b) by 17 days.

This patent is subject to a terminal disclaimer.

(21) Appl. No.: 13/885,024

(22) PCT Filed: Dec. 13, 2011

(86) PCT No.: PCT/EP2011/072628
§ 371 (c)(1), (2), (4) Date: May 13, 2013

(87) PCT Pub. No.: WO2012/080264
PCT Pub. Date: Jun. 21, 2012

(65) Prior Publication Data
US 2013/0237681 A1 Sep. 12, 2013

(30) Foreign Application Priority Data
Dec. 17, 2010 (EP) .................................. 10195795

(51) Int. Cl.
| | | |
|---|---|---|
| C07C 209/00 | (2006.01) | |
| C07C 229/00 | (2006.01) | |
| C07C 211/00 | (2006.01) | |
| C07C 215/00 | (2006.01) | |
| C08L 63/00 | (2006.01) | |
| C08G 18/18 | (2006.01) | |
| C08G 59/50 | (2006.01) | |
| C07C 213/08 | (2006.01) | |
| C07C 215/08 | (2006.01) | |
| C07C 209/26 | (2006.01) | |
| C07C 211/27 | (2006.01) | |
| C07C 213/02 | (2006.01) | |
| C07C 215/14 | (2006.01) | |
| C07C 219/06 | (2006.01) | |
| C07C 265/14 | (2006.01) | |

(52) U.S. Cl.
CPC .......... *C08G 18/1816* (2013.01); *C07C 209/26* (2013.01); *C07C 211/27* (2013.01); *C07C 213/02* (2013.01); *C07C 213/08* (2013.01); *C07C 215/08* (2013.01); *C07C 215/14* (2013.01); *C07C 219/06* (2013.01); *C07C 265/14* (2013.01); *C08G 59/504* (2013.01); *C08L 63/00* (2013.01)

(58) Field of Classification Search
CPC .................................................. C08G 18/1816
USPC .......................................................... 528/68
See application file for complete search history.

(56) References Cited

U.S. PATENT DOCUMENTS

| | | | |
|---|---|---|---|
| 2,828,339 A | 3/1958 | Caldwell et al. | |
| 3,236,895 A | 2/1966 | Lee et al. | |
| 4,126,640 A | 11/1978 | Floyd | |
| 4,132,702 A | 1/1979 | Schmidt et al. | |
| 4,160,036 A * | 7/1979 | Bradshaw et al. | 514/653 |
| 5,739,209 A | 4/1998 | Lassila et al. | |
| 6,262,096 B1 * | 7/2001 | Kim et al. | 514/369 |
| 7,402,585 B2 * | 7/2008 | Jung et al. | 514/266.23 |
| 2010/0048832 A1 * | 2/2010 | Vedage et al. | 525/453 |

FOREIGN PATENT DOCUMENTS

| | | |
|---|---|---|
| EP | 0 257 848 A2 | 3/1988 |
| EP | 0 438 695 A1 | 7/1991 |
| EP | 2 133 378 A1 | 12/2009 |
| JP | S50-134987 A | 10/1975 |
| JP | S63-48255 A | 2/1988 |
| WO | 01/89591 A2 | 11/2001 |
| WO | 2007/024836 A2 | 3/2007 |

OTHER PUBLICATIONS

International Preliminary Report on Patentability issued in International Application No. PCT/EP2011/072628 dated Jun. 18, 2013.
Lee et al., "Pentaerythritol fragmentation during conversion to a polyamine ligand-isolation of 1,1-bis(2'-aminoethylaminomethyl)-ethene," *Tetrahedron Letters*, 2010, pp. 4915-4917, vol. 51.
International Search Report issued in International Patent Application No. PCT/EP2011/072628 dated Feb. 15, 2012.
Database Caplus on STN, AN 2008:1383655, DN 149:575982 Baxter, E. W. et al., Reductive Aminations of Carbonyl Compounds with Borohydride and Borane Reducing Agents, Organic Reactions, 2002, 59.
Diaz, et al., "Activation of Urea as a Leaving Group in Substitution Reactions of Formamidine Ureas," Chemistry Letters, vol. 34, No. 1, (2005) pp. 78-79.
Li et al., "Synthesis and evaluation of bivalent, peptidomimetic antagonists of ?v?3 integrins," Bioorganic & Medicinal Chemistry Letters, 20 (2010) pp. 6577-6580.
Jul. 28, 2015 Office Action issued in Japanese Application No. 2013-543720.
Nov. 13, 2015 Office Action issued in Russian Application No. 2013117935/04.

* cited by examiner

*Primary Examiner* — David Karst
(74) *Attorney, Agent, or Firm* — Benjamin S. Prebyl

(57) ABSTRACT

The present invention relates to novel amides having secondary amino groups, a process for preparing them, adducts of these amines and their uses. The amides can be prepared in a simple way from readily available starting materials. They and their adducts have, in particular, a low viscosity and are suitable as constituent of polyurethane and polyurea compositions having excellent processability and high flexibility, and also as constituent of epoxy resin compositions, in particular coatings.

19 Claims, No Drawings

AMINES HAVING SECONDARY ALIPHATIC AMINO GROUPS

TECHNICAL FIELD

The present invention relates to novel amines and their use, in particular as curing agents in curable compounds which are based in particular on epoxies or isocyanates as well as curable compounds containing these amines and use therefore, in particular as coatings and paints.

STATE OF THE ART

Polyamines are often used as curing agents in curable compounds, in particular in epoxy resin and polyurethane or polyurea compositions. The amines generally used in epoxy resin compositions have a high primary amino group content, which reacts with carbon dioxide gas ($CO_2$) from the air and can form stable carbonate and carbamate salts. This leads first to the result that curing agents based on such amines cannot be stored in the open air because otherwise the material in the drums will form crusts. On the other hand, epoxy resin compositions prepared using such curing agents will also absorb $CO_2$ during and after application, which may lead to defects such as clouding, spots, rough or tacky surfaces to incomplete curing in particular in the case of coating applications. Such $CO_2$-related effects are referred to by those skilled in the art as "blushing." To reduce blushing effects and to dilute the preparation, benzyl alcohols is often added to the curing agents, but this in turn brings other disadvantages because benzyl alcohol is undesirable in many applications due to its volatility, and large quantities of benzyl alcohol will significantly reduce the mechanical properties of a fully cured epoxy resin. In polyurethane and polyurea compositions, polyols and amines are used as the curing agents. Polyols have the disadvantage that their reactivity to isocyanates is just as high as is the reactivity of isocyanates with water, which can lead to bubbling and foaming, to surface tackiness and to reduced adhesion and strength of the fully cured compound in the presence of high atmospheric humidity or in direct contact with water because of the release of $CO_2$ in the reaction of isocyanates with water. In addition, substantial quantities of catalysts must typically be added when using polyols to make the curing reaction fast enough at room temperature, but this can entail disadvantages with regard to the toxicity or stability of the compositions, for example. To avoid these problems, it is fundamentally attractive to use amines instead of polyols as curing agents because amines have a much higher reactivity with isocyanates and thus are hardly in competition with water and do not require any catalysts. However, the usual aliphatic amines are reacted with so many isocyanates that they can hardly be mixed adequately into a polyisocyanate even when using machinery equipment before the mixture becomes solid. This therefore results in inhomogeneous products that are unsatisfactory both visually and mechanically, and problems also occur with flow and wetting of the substrates. Although aromatic amines are less reactive, they are highly toxic and are not stable when exposed to light, so that compounds cured with them undergo yellowing quickly.

Of the aliphatic amines, those with mostly secondary amino groups are more hydrophobic and less reactive than those with mostly primary amino groups and they have hardly any tendency to blushing. Furthermore, they are less volatile in general and have less of an odor. Therefore they are attractive as curing agent in epoxy resin compositions as well as in polyurethane or polyurea compositions. Many of the known amines having mainly secondary amino groups are solid or have a high viscosity at room temperature, which interferes with their processability in curable compounds and necessitates the use of solvents to some extent, although that is undesirable for many applications. With regard to their reactivity and tolerability, the known amines having mainly secondary amino groups often do not meet the requirements of successful use in curable compounds based on epoxy resins or polyisocyanates.

Since a variety of amines having mainly primary amino groups are available commercially, it is an attractive way to synthesize amines having mainly secondary amino groups starting from these products.

A known method of obtaining secondary amino groups is the addition reaction of primary amino groups with Michael acceptors, in particular acrylonitrile, acrylic acid esters or maleic acid esters. These reagents are inexpensive and the reaction proceeds successfully even under mild conditions. However it is usually very slow and incomplete and thus leaves a portion of the Michael acceptors in unreacted form, which may necessitate their subsequent removal if an odor-free product is to be obtained. The use of esters as Michael acceptors may also lead to the formation of unwanted byproducts because ester groups may react with secondary and especially with primary amino groups to form amides. Therefore amines having ester groups synthesized in this way must be separated from unconverted fractions having primary amino groups in a complex purification process.

Another known method of obtaining secondary amino groups is by reductive alkylation of primary amino groups with ketones or aldehydes. Amines having mainly secondary amino groups synthesized by this method are described in U.S. Pat. No. 4,126,640, EP 0 438 695 and U.S. Pat. No. 5,739,209, for example. When ketones are used, these processes yield amines having secondary amino groups which have a strong steric hindrance and are usually less reactive. The aldehydes used in the state of the art may in turn lead to other problems. For example, simple aliphatic aldehydes such as formaldehyde or acetaldehyde tend to form unwanted byproducts due to overalkylation and formation of aminal whereas more strongly substituted aliphatic aldehydes such as isobutyraldehyde or 2-ethylhexanal yield products that often do not have adequate compatibility with epoxy resins. Amination may be incomplete when using benzaldehyde and other aromatic aldehydes because the benzyl group can be split off again under hydrogenation conditions.

There is thus a demand for amines which have secondary aliphatic amino groups and are liquid and have a low viscosity at room temperature while also having good compatibility with the epoxy resins and polyurethane and polyurea compositions but their reactivity with isocyanates is not too high.

SUMMARY OF THE INVENTION

The object of the present invention is therefore to make available novel amines having secondary aliphatic amino groups, which are simple to synthesize, can be used as curing agents in curable compounds, in particular those based on epoxy resins or polyisocyanates, which are not subject to the disadvantages of the amines known from the state of the art.

It has surprisingly been found that this problem is solved by amines according to claim 1. These are typically liquid compounds with a relatively low viscosity and a low volatility and very little odor. They have such a low reactivity with $CO_2$ that they can be stored in air without forming a crust or precipitation or having an increase in viscosity. Furthermore, they can be synthesized in high purity by reductive alkylation of commercial amines having primary amino groups with aldehydes, which have an aldehyde group on a tertiary carbon and one of the radicals described below, in a simple process that does not require any complex workup steps.

The amines according to claim 1 have good compatibility with epoxy resin as well as polyurethane and polyurea compositions. They are especially suitable as curing agents in epoxy resin coatings, which have very little blushing effect and in particular are free of solvents, benzyl alcohol and similar diluents. In addition, they are specifically suitable as curing agents in polyurethane and polyurea compositions, because they have a moderate reactivity with isocyanate groups and therefore form coatings which cure rapidly and have a processing speed that permits ease of handling.

Additional aspects of the present invention are the subject matter of additional independent claims. Especially preferred embodiments of the invention are the subject matter of the dependent claims.

Methods of Implementing the Invention

One subject matter of the present invention is an amine of formula (I)

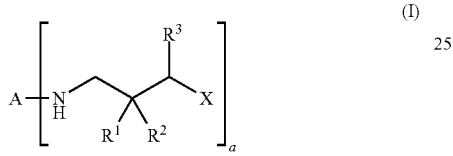

in which
A stands for the radical of an amine after removal of a primary aliphatic amino group;
a stands for an integer from 1 to 6, with the provision that in the case when a=1, the radical A has at least one reactive group selected from the group consisting of primary amino groups, secondary amino groups, hydroxyl groups, mercapto groups and silane groups;
$R^1$ and $R^2$ either
  independently of one another each stand for a monovalent hydrocarbon radical with 1 to 12 carbon atoms,
  or together they stand for a divalent hydrocarbon radical with 4 to 12 carbon atoms which is part of an optionally substituted carbocyclic ring with 5 to 8 carbon atoms, preferably 6 carbon atoms;
$R^3$ stands for a hydrogen atom or an alkyl group or an arylalkyl group or an alkoxycarbonyl group each with 1 to 12 carbon atoms, and
X stands for a radical selected from the group consisting of $X^a$, $X^b$, $X^c$ and $X^d$,
wherein
$X^a$ stands for —$OR^4$, where
  $R^4$ stands for a hydrogen atom or a hydrocarbon radical with 1 to 20 carbon atoms, which optionally has at least one heteroatom, in particular oxygen in the form of ether, carbonyl or ester groups;
$X^b$ stands for

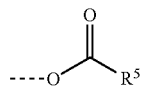

wherein
  $R^5$ stands for a hydrogen atom or a hydrocarbon radical with 1 to 20 carbon atoms, which optionally has at least one heteroatom, in particular oxygen in the form of ether, carbonyl or ester groups;
$X^c$ stands for

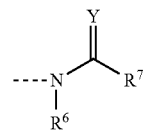

wherein
Y stands for O or S and
$R^6$ and $R^7$ either
  together stand for a divalent radical having 2 to 10 carbon atoms, optionally having oxygen atoms or sulfur atoms, this radical being part of an optionally substituted five- or six- or seven-membered ring,
  or
  $R^6$ stands for an alkyl, cyclo alkyl, aryl alkyl or acyl radical with 1 to 10 carbon atoms and
  $R^7$ stands for a hydrogen atom or a monovalent radical with 1 to 20 carbon atoms, selected from the group consisting of an alkyl radical, a cyclo alkyl radical, an aryl alkyl radical, an aryl radical, —$OR^8$, —$SR^8$ and —$NR^8R^9$,
    where $R^8$ and $R^9$ either each stand for a hydrocarbon radical or together stand for an alkylene radical, which is part of a five-, six- or seven-membered ring; and
$X^d$ stands for a substituted or unsubstituted aryl radical.

The dashes in the formulas in this document each represent a bond between a substituent and the respective molecular moiety.

An amine of formula (I) in which X stands for $X^a$ is an amine of formula (Ia); an amine of formula (I), in which X stands for $X^b$ is an amine of formula (Ib); an amine of formula (I) in which X stands for $X^c$ is an amine of formula (Ic); an amine of formula (I) in which X stands for $X^d$ is an amine of formula (Id).

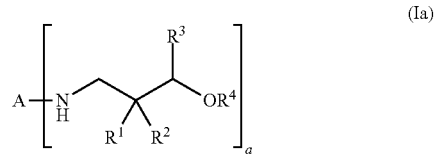

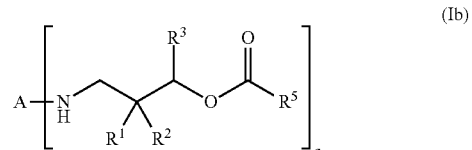

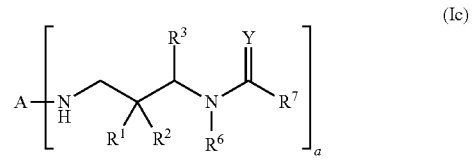

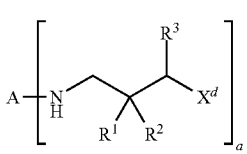

(Id)

In formulas (Ia) through (Id), A, a, $R^1$, $R^2$, $R^3$, $R^4$, $R^5$, $R^6$, $R^7$ and $X^d$ have the meanings already given above.

Substance names which begin with "poly" such as polyamine, polyol or polyepoxide are substances which formally contain two or more of the functional groups that occur in their name per molecule.

The term "primary amino group" refers to an $NH_2$ group bound to an organic radical; "secondary amino group" refers to an NH group bound to two organic radicals, which may also be a joint part of a ring, and "tertiary amino group" refers to an amino group whose nitrogen atom (tertiary amine nitrogen) is bound to three organic radicals, such that two of these radicals may also be joint parts of a ring.

The term "aliphatic" refers to an amine or an isocyanate whose amino or isocyanate groups are each bound to aliphatic, cycloaliphatic or araliphatic radicals; similarly these groups are also referred to as aliphatic amino groups or aliphatic isocyanate groups.

An amine or an isocyanate is referred to as "aromatic" when its amino groups or isocyanate groups are each bound to an aromatic radical. Accordingly, these groups are also referred to as aromatic amino groups or aromatic isocyanate groups.

A substance is referred to as a "primary aliphatic polyamine" if it formally has two or more primary aliphatic amino groups per molecule. A substance is referred to as a "secondary aliphatic polyamine" when it formally has two or more secondary aliphatic amino groups per molecule.

The silicon-containing group bound to the organic radical of an organo alkoxy silane is known as a "silane group". A silicon-containing compound in which the silicon atom has at least one, in particular two or three alkoxy groups and also a directly bound organic radical and thus has at least one Si—C bond is referred to as "organo alkoxy silane" or simply "slime."

The term "curable compound" comprises liquid or multiple reactive organic compounds and compositions thereof which are prepared at least partially by synthesis and can be cured either alone and/or by contact with air to form plastics and plastic compositions.

The term "curing agent" refers to compound having at least two reactive groups, for example, in the form of primary or secondary amino groups, hydroxyl groups or mercapto groups which may serve as reactants in the curing of curable compounds to form plastics.

The term "polymer" comprises, on the one hand, a group of macromolecules that are chemically uniform but differ with respect to the degree of polymerization, the molecular weight and chain length. these polymers are synthesized by a polyreaction (polymerization, polyaddition, polycondensation). On the other hand, the term also includes derivatives of such a group of macromolecules from polyreactions, thus compounds which are obtained by reactions such as additions or substitutions of functional groups on preselected macromolecules and which may be chemically uniform or chemically heterogeneous. The term additionally includes so-called prepolymers, i.e., reactive oligomeric preadducts, whose functional groups are involved in the synthesis of macromolecules.

"Room temperature" refers to a temperature of 23° C.

The term "tolerable" or "compatible" based on a curing agent of a curable compound refers to the circumstance that the curing agent can be incorporated more or less homogeneously into this composition and that no defects which can be attributed to separation phenomena such as in particular film clouding or surface disturbances in the form of markings, structures or bleeding are caused after its curing.

The designations indicated in bold type such as PA, ALD, Y1, Y2, Y3, VB, RG, AD, AD1, AD2, Z1, Z2, PUP, PI, HV, S or the like serve only to facilitate an understanding in reading and identification.

A preferably stands for a hydrocarbon radical that has a valence of "a" and has a molecular weight in the range of 28 to 10,000 g/mol, which optionally contains ether groups, amino groups, hydroxyl groups, mercapto groups or silane groups.

A especially preferably stands for an a-valent hydrocarbon radical with a molecular weight in the range of 28 to 10,000 g/mol, which optionally contains ether groups or primary or secondary amino groups.

a preferably stands for 1 to 3, especially preferably for 2 or 3.

$R^1$ and $R^2$ each preferably stands for a methyl radical.

$R^3$ preferably stands for a hydrogen atom.

$R^1$ and $R^2$ in particular thus each stand for a methyl radical and/or $R^3$ stands for a hydrogen atom.

$R^4$ preferably stands for a hydrogen atom or a hydrocarbon radical with 1 to 12 carbon atoms, optionally containing ether oxygen.

$R^5$ preferably stands for a hydrogen atom or a linear or branched alkyl radical with 1 to 11 carbon atoms, optionally with cyclic components and optionally with at least one heteroatom or for a mono- or polyunsaturated linear or branched hydrocarbon radical with 5 to 11 carbon atoms or for an optionally substituted aromatic or heteroaromatic six-membered ring.

$R^6$ preferably stands for a methyl, ethyl, propyl, isopropyl, butyl, 2-ethyl hexyl, cyclo hexyl, benzyl radical, and $R^7$ stands for a hydrogen atom or a methyl, ethyl, propyl, isopropyl, butyl, 2-ethyl hexyl, cyclo hexyl, benzyl, methoxy, ethoxy, propoxy or isopropoxy radical.

In addition, $R^6$ and $R^7$ together—including the nitrogen atom and the carbonyl and/or thiocarbonyl group—preferably form a ring, in particular a 2-pyrrolidone ring, a pyrrolidine-2,5-dione ring, a piperidin-2-one ring, a piperidine-2,6-dione ring, an azepan-2-one ring, an oxazolidin-2-one ring or a thiazolidin-2-one ring, wherein such a ring is optionally substituted.

$X^d$ preferably stands for a phenyl, biphenyl or naphthyl radical, this radical optionally being substituted, in particular with linear or branched alkyl radicals with 1 to 6 carbon atoms, with alkoxy groups with 1 to 6 carbon atoms, with ester groups with 1 to 6 carbon atoms or with nitrilo groups.

In particular $X^d$ stands for phenyl, 2-methylphenyl, 4-methylphenyl, 2,4-dimethylphenyl, 2,4,6-trimethylphenyl, 2-methoxyphenyl, 4-methoxyphenyl, 4-biphenyl, 1-naphthyl or 2-naphthyl.

$X^d$ most preferably stands for phenyl or 4-methylphenyl.

An amine of formula (I) may be synthesized by reductive alkylation of at least one amine PA of formula (II) with at least one aldehyde ALD of formula (III).

$$A\!-\!(\text{NH}_2)_a \quad (II)$$

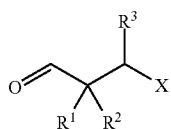

(III)

In formulas (II) and (III), A, a, $R^1$, $R^2$, $R^3$ and X have the meanings already given above.

The aldehyde ALD may be used in stoichiometric ratios or in stoichiometric excess with respect to the primary amino groups of the amine PA, which yields amines of formula (I) which are free of primary amino groups. If the amine PA has at least two primary amino groups, then the aldehyde ALD may also be used in a less than stoichiometric amount with respect to the primary amino groups of the amine PA. The resulting amines of formula (I) also contain primary amino groups in addition to secondary amino groups and optionally tertiary amino groups.

In particular an amine of formula (I) can be obtained by the condensation of at least one amine PA of formula (II) with at least one aldehyde ALD of formula (III) to yield an imine of formula (IV), which is then hydrogenated.

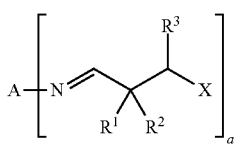

(IV)

A, a, $R^1$, $R^2$, $R^3$ and X in formula (IV) have the meanings given above.

An amine of formula (I) can be synthesized directly from the reactants in a one-pot reaction with hydrogenation. However, the imine of formula (IV) may also be isolated as an intermediate and purified, if necessary, and only then hydrogenated in a second reaction step. It is also known that the isolated imines of formula (IV) can also be used as crosslinking agents that are activated by moisture, so-called "blocked amines" or "latent curing agents," in curable compounds, in particular in single-component or two-component polyurethane compositions containing isocyanate groups.

The water released during condensation to form the imine of formula (IV) need not be removed but instead may remain in the reaction mixture during hydrogenation. After hydrogenation, the water may be removed by distillation, for example, optionally together with any solvent that is present.

The hydrogenation process to synthesize an amine of formula (I) may be performed directly with molecular hydrogen or indirectly by transfer of hydrogen from other reagents. Examples of such reagents includes formic acid, where $CO_2$ is released (based on a Leuckart-Wallach reaction); cyclohexene, which is dehydrogenated to benzene as well as other alkenes such as limonene; organosilanes; alkali metals in protic solvents or hydrazine in the presence of an oxidizing agent. The term "hydrogenation" as used here should also include reduction by means of hydrides such as lithium aluminum hydride, sodium borohydride and sodium bis(2-methoxy ethoxy)aluminum hydride (Vitride®, Red-Al®). Hydrogenation with molecular hydrogen is preferred.

The hydrogen required for hydrogenation is preferably used at an elevated pressure, in particular 5 to 250 bar, and an elevated temperature, in particular 20° C. to 160° C., in the presence of a suitable catalyst. The conditions are advantageously selected, so that on the one hand, the imino groups are hydrogenated as completely as possible, while on the other hand, no other constituents of the imine of formula (IV) are hydrogenated or decomposed, if possible.

Suitable catalysts for the hydrogenation include homogeneous catalysts, for example, rhodium, ruthenium or iridium complexes and in particular heterogeneous catalysts, for example, platinum, palladium, rhodium, ruthenium, osmium, rhenium, nickel, cobalt or iron as well as compounds or preparations thereof on carrier materials, where examples of suitable carrier materials include in particular pumice, diatomaceous earth, aluminum, silica gel or activated carbon. Especially suitable are palladium-on-carbon (Pd/C), platinum-on-carbon (Pt/C), Adams catalyst and Raney nickel. Palladium on carbon and platinum on carbon are the preferred catalysts.

The reductive alkylation is preferably performed in liquid phase. It may optionally be performed without a solvent or in the presence of a solvent, where suitable solvents are inert under the reaction conditions. In particular $C_1$ to $C_{10}$ alkanes, for example, hexane, heptane or cyclohexane and alcohols, in particular primary $C_1$ to $C_6$ alcohols, such as methanol or ethanol, as well as secondary alcohols such as isopropanol, and tertiary alcohols, such as tert-butanol, are especially suitable as the solvent.

The hydrogenation may be performed in a batch operation or in a continuous process, for example, in a continuously operating hydrogenation apparatus, where the substance to be hydrogenated, optionally in solution, is mixed with hydrogen continuously under pressure and is passed through a suitable catalyst. The hydrogen here may be generated continuously by electrolysis of water.

In a preferred process for synthesis of an amine of formula (I), at least one amine PA of formula (II), at least one aldehyde ALD of formula (III) and optionally at least one suitable solvent are mixed together, the reaction mixture is then hydrogenated by a suitable method and next the water released from the formation of imine is removed by applying a vacuum, optionally together with the solvent.

In an especially preferred method for synthesis of an amine of formula (I), at least one amine PA of formula (II), at least aldehyde ALD of formula (III) and optionally at least one suitable solvent are mixed together, the reaction mixture is then hydrogenated in a continuous process and next the water released in the formation of imine is removed, optionally together with the solvent, by applying a vacuum. The mixing of the amine PA and the aldehyde ALD of formulas (II) and (III) may be performed either in batches or also continuously.

In a first embodiment, suitable examples of the amine PA of formula (II) include primary aliphatic polyamines, which are known as curing agents in curable compounds containing epoxy groups or isocyanate groups, in particular the following:

aliphatic, cycloaliphatic or araliphatic primary diamines, such as in particular ethylene diamine, 1,2-propane diamine, 1,3-propane diamine, 2-methyl-1,2-propane diamine, 2,2-dimethyl-1,3-propane diamine, 1,3-butane diamine, 1,4-butane diamine, 1,3-pentane diamine (DAMP), 1,5-pentane diamine, 1,5-diamino-2-methyl-pentane (MPMD), 2-butyl-2-ethyl-1,5-pentane diamine (C11-neodiamine), 1,6-hexane diamine, 2,5-dimethyl- 1,6-hexane diamine, 2,2,4- and 2,4,4-trimethyl hexamethylene diamine (TMD), 1,7-heptane diamine, 1,8-octane diamine, 1,9-nonane diamine, 1,10-decane diamine, 1,11-undecane diamine, 1,12-dodecane diamine, 1,2-, 1,3- and 1,4-diamino cyclo hexane, bis-(4-amino cyclo hexyl) methane ($H_{12}$-MDA), bis-(4-amino-3-methyl cyclo hexyl) methane, bis-(4-amino-3-ethyl cyclohexyl) methane, bis-(4-amino-3,5-dimethyl cyclo hexyl) methane, bis-(4-amino-3-ethyl-5-methyl cyclohexyl) methane (M-MECA), 1-amino-3-amino methyl-3,5,5-trimethylcyclohexane (=isophorone diamine or IPDA), 2- and 4-methyl-1,3-diamino cyclo hexane and mixtures thereof, 1,3- and 1,4-bis-(amino methyl)cyclohexane, 2,5(2,6)-bis-(amino methyl) bicyclo[2.2.1]heptane (NBDA), 3(4),8(9)-bis-(amino methyl)-tricyclo[$5.2.1.0^{2,6}$]decane, 1,4-diamino-2,2,6-trimethyl cyclo hexane (TMCDA), 1,8-menthane diamine, 3,9-bis-(3-amino propyl)-2,4,8,10-tetraoxaspiro[5.5]undecane as well as 1,3- and 1,4-xylylene diamine; aliphatic, cycloaliphatic or araliphatic primary triamines such as 4-amino methyl-1,8-octane diamine, 1,3,5-tris-(amino methyl)benzene, 1,3,5-tris-(amino methyl) cyclo hexane, tris-(2-amino ethyl)amine, tris-(2-amino propyl)amine, tris-(3-amino propyl)amine; aliphatic primary diamines containing ether groups, such as in particular bis-(2-amino ethyl)ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxamidecane-1,13-diamine and higher oligomers of these diamines, bis-(3-amino propyl) poly tetrahydro furans and other poly tetrahydro furan diamines as well as polyoxy alkylene diamines. The latter are typically products of the amination of polyoxy alkylene diols and are obtainable in particular under the name Jeffamine® (from Huntsman), under the name polyether amines (from BASF) or under the name PC Amine® (from Nitroil). Particularly suitable polyoxy alkylene diamines include Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine® ED-2003, Jeffamine® XTJ-568, Jeffamine® XTJ-569, Jeffamine® XTJ-523, Jeffamine® XTJ-536, Jeffamine® XTJ-542, Jeffamine® XTJ-559, Jeffamine® EDR-104, Jeffamine® EDR-148, Jeffamine® EDR-176; polyether amine D 230, polyether amine D 400 and polyether amine D 2000, PC Amine® DA 250, PC Amine® DA 400, PC Amine® DA 650 and PC Amine® DA 2000;

primary polyoxy alkylene triamines which are typically products of the amination of polyoxy alkylene triols and available, for example, under the name Jeffamine® (from Huntsman), under the name polyether amines (from BASF) or under the name PC Amine® (from Nitroil), such as in particular Jeffamine® T-403, Jeffamine® T-3000, Jeffamine® T-5000, polyether amine T 403, polyether amine T 5000 and PC Amine® TA 403;

tertiary polyamines having amino groups with two primary aliphatic amino groups such as in particular N,N'-bis-(amino propyl) piperazine, N,N-bis-(3-amino propyl) methyl amine, N,N-bis-(3-amino propyl)ethyl amine, N,N-bis-(3-amino propyl) propyl amine, N,N-bis-(3-amino propyl)cyclo hexyl amine, N,N-bis-(3-amino propyl)-2-ethylhexyl amine as well as the products of double cyanoethylation and subsequent reduction of fatty amines which are derived from natural fatty acids such as N,N-bis-(3-amino propyl) dodecyl amine and N,N-bis-(3-amino propyl) tallow alkyl amine obtainable as Triameen® Y12D and Triameen® YT (from Akzo Nobel);

polyamines having tertiary amino groups with three primary aliphatic amino groups, such as in particular tris-(2-amino ethyl)amine, tris-(2-amino propyl)amine and tris-(3-amino propyl)amine;

polyamines having secondary amino groups with two primary aliphatic amino groups such as in particular 3-(2-amino ethyl) amino propyl amine, bis-hexamethylene triamine (BHMT), diethylene triamine (DETA), triethylene tetramine (TETA), tetraethylene pentamine (TEPA), pentaethylene hexamine (PEHA) and higher homologs of linear polyethylene amines such as polyethylene polyamine with 5 to 7 ethylene amine units (so-called "higher ethylene polyamine" or HEPA), products from multiple cyanoethylation or cyanobutylation and then hydrogenation of primary di- and polyamines having at least two primary amino groups, such as dipropylene triamine (DPTA), N-(2-amino ethyl)-1,3-propane diamine (N3 amine), N,N-bis(3-aminopropyl)-ethylene diamine (N4 amine), N,N'-bis-(3-aminopropyl)-1,4-diamino butane, N5-(3-aminopropyl)-2-methyl-1,5-pentane diamine, N3-(3-aminopentyl)-1,3-pentane diamine, N5-(3-amino-1-ethylpropyl)-2-methyl-1,5-pentane diamine and N,N'-bis-(3-amino-1-ethylpropyl)-2-methyl-1,5-pentane diamine.

In another embodiment, amines having only one primary aliphatic amino group and at least one additional reactive group selected from the group consisting of secondary amino groups, hydroxyl groups, mercapto groups and silane groups are suitable as the amine PA of formula (II).

Examples of suitable amines having a primary aliphatic amino group and at least one secondary amino group include in particular N-methyl-1,2-ethane diamine, ethane diamine, N-butyl-1,2-ethane diamine, N-hexyl-1,2-ethane diamine, N-(2-ethylhexyl)-1,2-ethane diamine, N-cyclohexyl-1,2-ethane diamine, 4-amino methyl piperidine, 3-(4-amino butyl) piperidine, N-(2-amino ethyl) piperazine, N-(2-aminopropyl)piperazine, $N^1$-(3-(dimethylamino)propyl)-1,3-diaminopropane (DMAPAPA), $N^1$-(2-(dimethyl amino)ethyl) propane-1,3-diamine, diamines from cyanoethylation or cyanobutylation and then hydrogenation of primary monoamines, for example, N-methyl-1,3-propane diamine, N-ethyl-1,3-propane diamine, N-butyl-1,3-propane diamine, N-hexyl-1,3-propane diamine, N-(2-ethylhexyl)-1,3-propane diamine, N-dodecyl-1,3-propane diamine, N-cyclohexyl-1,3-propane diamine, 3-methyl amino-1-pentyl amine, 3-ethyl amino-1-pentyl amine, 3-butylamino-1-pentyl amine, 3-hexyl amino-1-pentyl amine, 3-(2-ethylhexyl) amino-1-pentyl amine, 3-dodecylamino-1-pentyl amine, 3-cyclo hexyl amino-1-pentyl amine and fatty diamines such as N-cocoalkyl-1,3-propane diamine, N-oleyl-1,3-propane diamine, N-soy alkyl-1,3-propane diamine, N-tallow alkyl-1,3-propane diamine or N—($C_{16-22}$-alkyl)-1,3-propane diamine such as those available commercially, for example, under the brand name Duomeen® from Akzo Nobel; triamines and tetramines derived from fatty amines such as coco alkyl dipropylene triamine, oleyl dipropylene triamine, tallow alkyl dipropylene triamine, oleyltripropylene tetramine and tallow alkyl tripropylene tetramine obtainable, for example, as Triameen® C, Triameen® OV, Triameen® T, Tetrameen® OV and Tetrameen® T (Akzo Nobel); the products of a Michael-type addition reaction of primary aliphatic diamines with acrylonitrile, maleic or fumaric acid diesters, citraconic acid diesters, acrylic and methacrylic acid esters, acrylic and methacrylic acid amides and itaconic acid diesters, reacted in a 1:1 molar ratio.

Examples of suitable amines having a primary aliphatic amino group and at least one hydroxyl group include in particular 2-amino ethanol, 2-amino-1-propanol, 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol and higher homologs thereof, aminopropyldiethanol amine (APDEA), 4-(2-amino ethyl)-2-hydroxyethylbenzene, 3-amino methyl-3,5,5-trimethylcyclohexanol, derivatives of glycols having a primary amino group such as diethylene glycol, dipropylene glycol, dibutylene glycol and higher oligomers and polymers of these glycols, in particular 2-(2-amino ethoxy) ethanol, 2-(2-(2-amino ethoxy)ethoxy) ethanol, α-(2-hydroxymethylethyl)-ω-(2-amino methyl ethoxy)poly (oxy(methyl-1,2-ethane diyl)); derivatives of polyalkoxylated trivalent or higher-valent alcohols having one hydroxyl group and one primary amino group; products of simple cyanoethylation followed by hydrogenation of glycols, in particular 3-(2-hydroxy ethoxy) propyl amine, 3(2-(2-hydroxyethoxy)ethoxy)propyl amine and 3-(6-hydroxy hexyloxy) propyl amine; as well as, in addition, aliphatic amines having one primary and one secondary amino group and one hydroxyl group, such as in particular N-hydroxy ethyl-1,3-propane diamine, N-hydroxy propyl-1,3-propane diamine and N3-hydroxy ethyl-1,3-pentane diamine.

Suitable amines having one primary aliphatic amino group and at least one mercapto group include in particular 2-amino ethane thiol (cysteamine), 3-aminopropane thiol, 4-amino-1-butane thiol, 6-amino-1-hexane thiol, 8-amino-1-octane thiol, 10-amino-1-decane thiol and 12-amino-1-dodecane thiol.

Suitable amines having one primary aliphatic amino group and one silane group include in particular 3-amino propyl trimethoxy silane, 3-amino propyl dimethoxy methyl silane, N-(2-amino ethyl)-3-amino propyl trimethoxy silane, N-(2-amino ethyl)-3-aminopropyl methyl dimethoxy silane, N-(2-amino ethyl)-N'-[3-(trimethoxy silyl) propyl]ethylene diamine, 3-amino-2-methyl propyl trimethoxy silane, 4-aminobutyl trimethoxy silane, 4-aminobutyl dimethoxy methyl silane, 4-amino-3-methyl butyl trimethoxy silane, 4-amino-3,3-dimethyl butyl trimethoxy silane, 4-amino-3,3-dimethyl butyl dimethoxy methyl silane, 2-amino ethyl trimethoxy silane, 2-amino ethyl dimethoxy methyl silane, amino methyl trimethoxy silane, amino methyl dimethoxy methyl silane, amino methylmethoxy dimethyl silane, 7-amino-4-oxaheptyl dimethoxy methyl silane as well as their analogs with ethoxy or isopropoxy groups instead of the methoxy groups on the silicon.

Primary aliphatic polyamines are preferred as the amine PA of formula (II).

The amine PA of formula (II) is especially selected from the group consisting of 1,5-diamino-2-methylpentane (MPMD), 2-butyl-2-ethyl-1,5-pentane diamine (C11-neodiamine), 1,6-hexane diamine, 2,5-dimethyl-1,6-hexane diamine, 2,2,4- and 2,4,4-trimethylhexamethylene diamine (TMD), 1,12-dodecane diamine, 1,4-diaminocyclohexane, bis-(4-aminocyclohexyl)methane (H$_{12}$-MDA), bis-(4-amino-3-methylcyclohexyl)methane, 1-amino-3-amino methyl-3,5,5-trimethylcyclohexane (=isophorone diamine or IPDA), 1,3-bis-(amino methyl)cyclohexane, 2,5(2,6)-bis-(amino methyl)bicyclo[2.2.1]heptane (NBDA), 3(4),8(9)-bis-(amino methyl)tricyclo[5.2.1.0$^{2,6}$]decane, 1,3-xylylene diamine, bis-hexamethylene triamine (BHMT), diethylene triamine (DETA), triethylene tetramine (TETA), tetraethylene pentamine (TEPA), pentaethylene hexamine (PEHA), polyethylene polyamine with 5 to 7 ethylene amine units (so-called "higher ethylene polyamines" or HPEA), dipropylene triamine (DPTA), N-(2-amino ethyl)-1,3-propane diamine (N3-amine), N,N'-bis(3-aminopropyl)ethylene diamine (N4-amine), polyoxy alkylene diamines and polyoxy alkylene triamines in particular with a molecular weight of 200 to 6000 g/mol in particular the commercial products Jeffamine® D-230, Jeffamine® D-400, Jeffamine® D-2000, Jeffamine® D-4000, Jeffamine® T-403, Jeffamine® T-3000 and Jeffamine® T-5000 (from Huntsman).

Aldehydes ALD of formula (III a) are suitable for synthesis of amines of formula (I a)

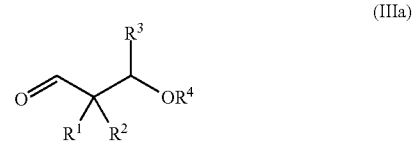

(IIIa)

In formula (III a), R$^1$, R$^2$, R$^3$ and R$^4$ have the meanings already given above.

For the case when R$^4$ in formula (III a) stands for a hydrogen atom, these are aliphatic, cycloaliphatic or araliphatic 2,2-disubstituted 3-hydroxyaldehyde such as in particular 2,2-dimethyl-3-hydroxy propanal, 2-hydroxymethyl-2-methyl butanal, 2-hydroxymethyl-2-ethyl butanal, 2-hydroxymethyl-2-methyl pentanal, 2-hydroxymethyl-2-ethyl hexanal, 1-hydroxymethyl cyclopentane carboxaldehyde, 1-hydroxymethyl-cyclohexane carboxaldehyde, 1-hydroxymethyl cyclohex-3-ene carboxaldehyde, 2-hydroxymethyl-2-methyl-3-phenyl propanal, 3-hydroxy-2-methyl-2-phenyl propanal and 3-hydroxy-2,2-diphenyl propanal. Such aldehydes are obtainable by Aldol reactions, in particular crossed Aldol reactions between primary or secondary aliphatic aldehydes, in particular formaldehyde and secondary aliphatic, secondary araliphatic or secondary cycloaliphatic aldehydes, for example, isobutyraldehyde, 2-methyl butyraldehyde, 2-ethyl butyraldehyde, 2-methyl valeraldehyde, 2-ethyl caproaldehyde, cyclopentane carboxaldehyde, cyclohexane carboxaldehyde, 1,2,3,6-tetrahydro benzaldehyde, 2-methyl-3-phenyl propionaldehyde, 2-phenyl propionaldehyde (hydratropaldehyde) or diphenyl acetaldehyde. 2,2-Dimethyl-3-hydroxy propanal 3-hydroxy pivalaldehyde) is preferred.

Additional aldehydes ALD of formula (III a) include ethers of the 2,2-disubstituted 3-hydroxyaldehydes mentioned above with alcohols or phenols of formula R$^4$—OH. Preferred aldehydes ALD of formula (III a) include 2,2-dimethyl-3-methoxy propanal, 2,2-dimethyl-3-ethoxy propanal, 2,2-dimethyl-3-propoxy propanal, 3-butoxy-2,2-dimethyl propanal, 2,2-dimethyl-3-pentoxy propanal, 2,2-dimethyl-3-hexoxy propanal where all the isomeric propoxy, butoxy, pentoxy and hexoxy groups are also included, 2,2-dimethyl-3-phenoxy propanal, 3-cyclohexyloxy-2,2-dimethyl propanal, 2,2-dimethyl-3-(2-ethylhexyloxy) propanal and 2,2-dimethyl-3-lauroxy propanal.

For synthesis of amines of formula (I b), aldehydes ALD of formula (III b) are suitable.

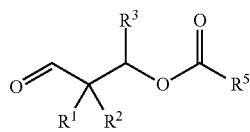 (IIIb)

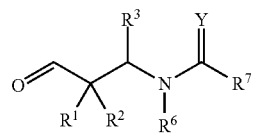 (IIIc)

In formula (III b), $R^1$, $R^2$, $R^3$ and $R^5$ each have the meanings already given above.

The aldehydes ALD of formula (III b) are esters of aliphatic, cycloaliphatic or araliphatic 2,2-disubstituted 3-hydroxyaldehydes, such as those mentioned above, with suitable carboxylic acids, where the following carboxylic acids are especially suitable: saturated aliphatic carboxylic acids such as in particular formic acid, acetic acid, propionic acid, butyric acid, isobutyric acid, valeric acid, caproic acid, 2-ethyl caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid; mono-unsaturated aliphatic carboxylic acids such as palmitoleic acid, oleic acid; polyunsaturated aliphatic carboxylic acids such as linoleic acid, linolenic acid, eleostearic acid, arachidonic acid; cycloaliphatic carboxylic acids such as cyclohexane carboxylic acid; araliphatic carboxylic acids such as phenyl acetic acid; aromatic carboxylic acids such as benzoic acid, naphthoic acid, toluoylic acid, anisic acid; isomers of these acids; fatty acid mixtures of the industrial saponification of natural oils and fats such as, for example, rapeseed oil, sunflower oil, linseed oil, oil tree oil, coconut oil, oil palm kernel oil and oil palm oil; as well as dicarboxylic acid monoalkyl and aryl esters such as those obtained from simple esterification of dicarboxylic acids such as succinic acid, glutaric acid, adipic acid, pimelic acid, suberic acid, azelaic acid, sebacic acid, 1,12-dodecanedioic acid, maleic acid, fumaric acid, hexahydro phthalic acid, hexahydro isophthalic acid, hexahydro-terephthalic acid, 3,6,9-trioxaundecanedioic acid and similar derivatives of polyethylene glycols with alcohols such as methanol, ethanol, propanol, butanol, higher homologs and isomers of these alcohols. Carboxylic acids with up to 12 carbon atoms are preferred, in particular formic acid, acetic acid, propionic acid, butyric acid, isobutyric acid, valeric acid, caproic acid, 2-ethylcaproic acid, caprylic acid, capric acid, lauric acid, cyclohexane carboxylic acid and benzoic acid. Preferred aldehydes ALD of formula (III b) include 2,2-dimethyl-3-formoyloxy propanal, 3-acetoxy-2,2-dimethyl propanal, 2,2-dimethyl-3-propionyloxy propanal, 3-butyroxy-2,2-dimethyl propanal, 2,2-dimethyl-3-isobutyroxy propanal, 2,2-dimethyl-3-valeroyloxy propanal, 2,2-dimethyl-3-hexanoyloxy propanal, 2,2 dimethyl-3-(2-ethylhexanoyloxy) propanal, 2,2-dimethyl-3-octanoyloxy propanal, 3-decanoyloxy-2,2-dimethyl propanal, 2,2-dimethyl-3-lauroyloxy propanal, 3-cyclohexanoyloxy-2,2-dimethyl propanal and 3-benzoyloxy-2,2-dimethyl propanal.

To synthesize amines of formula (I c), aldehydes ALD of formula (III c) are suitable.

In formula (III c) $R^1$, $R^2$, $R^3$, $R^6$ and $R^7$ have the meanings already given.

The aldehydes ALD of formula (III c) have amide, thioamide, urea, thiourea, urethane or thiourethane groups. They may be synthesized either directly or by way of a suitable intermediate.

In one embodiment an aldehyde ALD of formula (III c) is obtainable as the product of an α-aminoalkylation process which is similar to the Mannich reaction, as is known from the technical literature. An aldehyde Y1 of formula (V), an aldehyde Y2 of formula (VI) and a compound of formula (VII) are then reacted, splitting off water to form an aldehyde ALD of formula (III c).

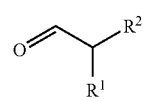 (V)

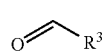 (VI)

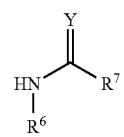 (VII)

In formulas (V), (VI) and (VII), Y, $R^1$, $R^2$, $R^3$, $R^6$ and $R^7$ have the meanings already given above.

This reaction may be carried out either with the free reagents of formulas (V), (VI) and (VII) or the reagents may be used partially or completely in derivatized form. In a preferred embodiment the reaction is carried out with all reagents in free form as a one pot reaction and the aldehyde ALD is purified by distillation after the reaction. Preferably no organic solvents are used in this process.

Suitable aldehydes Y1 of formula (V) include in particular isobutyraldehyde, 2-methyl butyraldehyde, 2-ethyl butyraldehyde, 2-methyl valeraldehyde, 2-ethyl caproaldehyde, cyclopentane carboxaldehyde, cyclohexane carboxaldehyde, 1,2,3,6-tetrahydrobenzaldehyde, 2-methyl-3-phenyl propionaldehyde, 2-phenyl propionaldehyde and diphenylacetaldehyde. Isobutyraldehyde is preferred.

Suitable examples of aldehyde Y2 of formula (VI) include in particular formaldehyde, acetaldehyde, propionaldehyde, butyraldehyde, isobutyraldehyde, phenylacetaldehyde and glyoxylic acid esters, in particular glyoxylic acid ethyl ester. Formaldehyde is preferred.

Suitable examples of the compound of formula (VII) include, on the one hand, amides, in particular N-methylformamide, N-ethyl formamide, N-butyl formamide, N-methyl acetamide, N-ethyl acetamide, N-isopropyl acetamide, N-butyl acetamide, N,N-(2-ethylhexyl) acetamide, cyclohexyl acetamide, N-benzyl acetamide, N-methyl propionamide, N-methyl butyramide, N-methyl-2-ethyl caproamide, N-methylbenzamide; in addition, lactams and derivatives thereof, in particular 2-pyrrolidone, 5-methyl-2-pyrrolidone, piperidin-2-one, ☐-caprolactam, 2-azabicyclo[2.2.1]hept-5-en-3-one; in addition, carbamates with a mono substitution on the nitrogen atom and derivatives thereof in particular O-ethyl-N-methyl carbamate, O-ethyl-N-ethyl carbamate, O-ethyl-N-propyl carbamate, O-methyl-N-ethyl carbamate, O-methyl-N-propyl carbamate, O-methyl-N-butyl carbamate, acetyl urethane, N-butyl urethane, oxazolidin-2-one, oxazolidine-2,5-dione; in addition, imides and derivatives thereof in particular pyrrolidine-2,5-dione succinic acid imide), 3,4-dimethyl pyrrolidine-2,5-dione, 3,3,4,4-tetramethylpyrrolidine-2,5-dione, 3-ethyl-3-methyl pyrrolidine-2,5-dione, piperidine-2,6-dione, 4,4-dimethyl piperidine-2,6-dione, 1,5,5-trimethyl imidazolidine-2,4-dione, phthalimide, methyl phthalimide, hexahydro phthalimide, methylhexahydro phthalimide, 5,5-dimethyl-1,3-oxazolidine-2,4-dione, acetimide; in addition to the above compounds, similar substances with sulfur atoms instead of oxygen atoms, in particular N-methyl thioacetamide, N-butyl thioacetamide, N-(2-ethylhexyl)thioacetamide, N-benzyl thioacetamide, N-methyl butyrthioamide, N-methyl-(2-ethyl capronthioamide), N-methyl benzthioamide, 2-thiopyrrolidone, O-ethyl-N-methyl thiocarbamate, S-ethyl-N-methyl thiocarbamate, O-methyl-N-ethyl thiocarbamate, thiazolidin-2-one and thiazolidine-2,5-dione.

The compound of formula (VII) is preferably selected from the group consisting of N-methyl formamide, N-methyl acetamide, N-butyl acetamide, N-(2-ethylhexyl) acetamide, N-benzyl acetamide, N-methyl butyramide, N-methyl-(2-ethylcapronamide), N-methyl benzamide, O-ethyl-N-methyl carbamate, 2-Pyrrolidone, piperidin-2-one, ☐-caprolactam, oxazolidin-2-one, thiazolidin-2-one, pyrrolidine-2,5-dione and phthalimide.

In another embodiment, an aldehyde ALD of formula (III c) is obtainable by starting with an intermediate in the form of an aldehyde Y3 of formula (VIII).

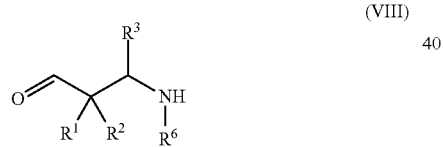

(VIII)

In formula (VIII), $R^1$, $R^2$, $R^3$ and $R^6$ have the meanings already given above.

An aldehyde Y3 of formula (VIII) is also obtainable as the product of an α-aminoalkylation process similar to the Mannich reaction in the same way as that already described for an aldehyde ALP of formula (III c), starting from the aldehydes Y1 and Y2 mentioned above, but using a primary amine $R^6$—$NH_2$ instead of the compound of formula (VII), wherein $R^6$ has the meanings already given above, and the aldehydes Y1 and Y2 and the primary amine are used approximately in a 1:1:1 molar ratio. Suitable examples of the primary amine $R^6$—$NH_2$ include in particular primary aliphatic amities, in particular methyl amine, ethyl amine, propyl amine, isopropyl amine, butyl amine, isobutyl amine, sec-butyl amine, hexyl amine, cyclohexyl amine, octyl amine, 2-ethyl-1-hexyl amine, benzyl amine, 1- or 2-phenylethyl amine and decyl amine.

To synthesize an aldehyde ALD of formula (III c), the aldehyde Y3 of formula (VIII) may ultimately be reacted with a suitable compound, in particular as described below:
  with a carboxylic acid, preferably in the form of a carboxylic acid chloride, ester or anhydride to yield the corresponding amide, where suitable carboxylic acids include saturated aliphatic or cycloaliphatic carboxylic acids such as in particular formic acid, acetic acid, propionic acid, butyric acid, isobutyric acid, valeric acid, isovaleric acid, pivalic acid, caproic acid, cyclohexane carboxylic acid, enanthic acid, caprylic acid, 2-ethylhexanoic acid, pelargonic acid, capric acid, neodecanoic acid, undecanoic acid, lauric acid, tridecanoic acid, myristic acid, pentadecanoic acid, palmitic acid, margaric acid, stearic acid, isostearic acid and arachic acid; mono- or polyunsaturated aliphatic carboxylic acids such as in particular palmitoleic acid, oleic acid, erucaic acid, sorbic acid, linoleic acid, linolenic acid, eleostearic acid, ricinoleic acid and ricinic acid; aromatic carboxylic acids such as in particular benzoic acid and the positional isomeric tolylic acids, methoxybenzoic acids and nitrobenzoic acids as well as chloride, esters and anhydrides of the dicarboxylic acids mentioned above, such as phthalic anhydride, 4-methylphthalic anhydride, succinic anhydride, maleic anhydride, citraconic anhydride, hexahydrophthalic acid, 4-methylhexahydrophthalic anhydride and 1,2,3,6-tetrahydrophthalic anhydride;

with a carbonate or preferably a chloroformic acid esters, such as in particular methyl, ethyl, propyl, isopropyl, butyl, isobutyl, neopentyl, hexyl, octyl, 2-ethylhexyl, benzyl, phenyl, tolyl and methoxyphenylchloroformate to form the corresponding urethane;

with an N,N-disubstituted carbamate or an N,N-disubstituted carbamic acid chloride such as in particular N,N-dimethyl, N,N-diethyl, N,N-diisopropyl, N,N-dibutyl, N-methyl-N-phenyl and N,N-diphenyl carbamoyl chloride as well as in particular 1-pyrrolidine, 1-piperidine, 1-morpholine and 4-methyl-1-piperazine carbonyl chloride to form the corresponding urea;

with a thiocarboxylic acid such as in particular thioacetic acid, thiopropionic acid, thiobenzoic acid, thiotolylic acid or phenyl thioacetic acid, preferably in the form of an acid chloride, acid ester or anhydride to form the corresponding thioamide or with a (di)thiocarbonate, a chloro(di)thioformic acid ester, an N,N-disubstituted thiocarbamate or an N,N-disubstituted carbamic acid chloride such as in particular O-methyl, O-ethyl, O-phenyl or O-p-tolylchlorido thiocarbonate, S-methyl, S-ethyl, S-propyl or S-phenylchlorido thiocarbonate, phenylchlorido dithiocarbonate, N,N-dimethyl, N,N-diethyl, N-methyl-N-phenyl or N,N-diphenylthiocarbamoyl chloride to form the corresponding (di)thiourethane or (di)thiourea.

Another possibility of synthesis of an aldehyde ALD of formula (III c) is by the reaction of an aldehyde Y1 of formula (V) as already defined above with a compound of formula (IX)

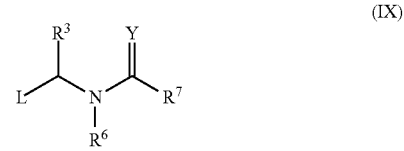

(IX)

wherein

L stands for a radical selected from the group consisting of a halogen atom, an alkoxy group, a carboxylic acid ester group, a urethane group bound by the nitrogen, a dialkylamino group and a di- or trialkyl ammonium group, and Y, $R^3$, $R^6$ and $R^7$ have the meanings already given above.

Suitable examples of compounds of formula (IX) include in particular N-chloromethyl or N-bromomethyl N-alkyl carbamates such as N-chloromethyl N-methylcarbamic acid ethyl ester as well as N-bromomethyl imides such as N-bromomethyl phthalimide and N-bromomethylpyrrolidine-2,5-dione.

Preferred aldehydes ALD of formula (III c) include N-(2,2-dimethyl-3-oxopropyl) N-methylformamide, N-(2,2-dimethyl-3-oxopropyl) N-methyl acetamide, N-(2,2-dimethyl-3-oxopropyl) N-butyl acetamide, N-(2,2-dimethyl-3-oxopropyl) N-(2-ethylhexyl) acetamide, N-(2,2-dimethyl-3-oxopropyl) N-benzyl acetamide, N-(2,2-dimethyl-3-oxopropyl) N-methyl butyramide, N-(2,2-dimethyl-3-oxopropyl) N-methyl-(2-ethyl caproamide), N-(2,2-dimethyl-3-oxopropyl)-N-methyl benzamide, O-ethyl-N-(2,2-dimethyl-3-oxopropyl) N-methyl carbamate, N-(2,2-dimethyl-3-oxopropyl)pyrrolidin-2-one, N-(2,2-dimethyl-3-oxopropyl) piperidin-2-one, N-(2,2-dimethyl-3-oxopropyl) azepan-2-one, N-(2,2-dimethyl-3-oxopropyl) oxazolidin-2-one, N-(2,2-dimethyl-3-oxopropyl)thiazolidin-2-one, N-(2,2-dimethyl-3-oxopropyl)pyrrolidine-2,5-dione and N-(2,2-dimethyl-3-oxopropyl) phthalimide.

For synthesis of amines of formula (Id) aldehydes ALD of formula (III d) are suitable.

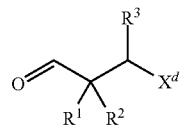

(III d)

$R^1$, $R^2$, $R^3$ and $X^d$ in formula (III d) have the meanings already given above.

Aldehydes ALD of formula (III d) are obtainable in particular from the base-catalyzed reaction of an aldehyde Y1 of formula (V) as already defined above with a compound of formula (X).

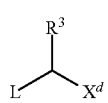

(X)

$R^3$, $X^d$ and L in formula (X) have the meanings already given above.

Suitable compounds of formula (X) include in particular chloromethyl- or bromomethyl-substituted aromatics such as in particular benzyl chloride, 2-methylbenzyl chloride, 4-methylbenzyl chloride, 2,4,6-trimethylbenzyl chloride, 4-chloromethylbenzoic acid ethyl ester, 2-, 3- and 4-methoxybenzyl chloride, 2-, 3- and 4-chloromethylbenzonitrile, 4-chloromethyl biphenyl, 1- and 2-(chloromethyl) naphthalene, 9-chloromethyl anthracene as well as the corresponding compounds with bromine instead of chlorine.

Preferred aldehydes ALD of formula (III d) include 2,2-dimethyl-3-phenylpropanol and 2,2-dimethyl-3-p-toluoyl propanal.

The aldehyde ALD of formula (III) is preferably selected from the group comprised of 2,2-dimethyl-3-hydroxy propanal, 2,2-dimethyl-3-methoxy propanal, 2,2-dimethyl-3-ethoxy propanal, 2,2-dimethyl-3-propoxy propanal, 3-butoxy-2,2-dimethyl propanal, 2,2-dimethyl-3-pentoxy propanal, 2,2-dimethyl-3-hexoxy propanal where the isomeric propoxy, butoxy, pentoxy and hexoxy groups are also intended, 2,2-dimethyl-3-phenoxy propanal, 3-cyclohexyloxy-2,2-dimethyl propanal, 2,2-dimethyl-3-(2-ethylhexyloxy) propanal, 2,2-dimethyl-3-lauroxy propanal, 2,2-dimethyl-3-formoyloxy propanal, 3-acetoxy-2,2-dimethyl propanal, 2,2-dimethyl-3-propionyloxy propanal, 3-butyroxy-2,2-dimethyl propanal, 2,2-dimethyl-3-isobutyroxy propanal, 2,2-dimethyl-3-valeroyloxy propanal, 2,2-dimethyl-3-hexanoyloxy propanal, 2,2-dimethyl-3-(2-ethylhexanoyloxy) propanal, 2,2-dimethyl-3-octanoyloxy propanal, 3-decanoyloxy-2,2-dimethyl propanal, 2,2-dimethyl-3-lauroyloxy propanal, 3-cyclohexanoyloxy-2,2-dimethyl propanal, 3-benzoyloxy-2,2-dimethyl propanal, N-(2,2-dimethyl-3-oxopropyl)-N-methylformamide, N-(2,2-dimethyl-3-oxopropyl) N-methyl acetamide, N-(2,2-dimethyl-3-oxopropyl)-N-butylacetamide, N-(2,2-dimethyl-3-oxopropyl) N-(2-ethylhexyl) acetamide, N-(2,2-dimethyl-3-oxopropyl)-N-benzylacetamide, N-(2,2-dimethyl-3-oxopropyl)-N-methyl butyramide, N-(2,2-dimethyl-3-oxopropyl) N-methyl-(2-ethyl caproamide), N-(2,2-dimethyl-3-oxopropyl)-N-methylbenzamide, O-ethyl-N-(2,2-dimethyl-3-oxopropyl) N-methyl carbamate, N-(2,2-dimethyl-3-oxopropyl)-pyrrolidin-2-one, N-(2,2-dimethyl-3-oxopropyl) piperidin-2-one, N-(2,2-dimethyl-3-oxopropyl) azepan-2-one, N-(2,2-dimethyl-3-oxopropyl) oxazolidin-2-one, N-(2,2-dimethyl-3-oxopropyl) thiazolidin-2-one, N-(2,2-dimethyl-3-oxopropyl)pyrrolidine-2,5-dione, N-(2,2-dimethyl-3-oxopropyl) phthalimide, 2,2-dimethyl-3-phenyl propanal and 2,2-dimethyl-3-p-toluoyl propanal.

The aldehyde ALD of formula (III) is preferably selected from the group comprised of 2,2-dimethyl-3-hydroxy propanal, 2,2-dimethyl-3-methoxy propanal, 3-acetoxy-2,2-dimethyl propanal, 2,2-dimethyl-3-isobutyroxy propanal, 2,2-dimethyl-3-lauroyloxy propanal, 3-benzoyloxy-2,2-dimethyl propanal, N-(2,2-dimethyl-3-oxopropyl)-N-methylacetamide and 2,2-dimethyl-3-phenyl propanal.

Another possibility for synthesis of an amine of formula (I c) starts from an intermediate in the form of an imine of formula (XI) rather than starting with an aldehyde ALD of formula (III c).

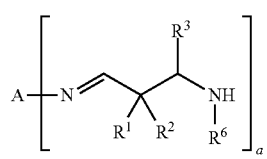

(XI)

In formula (XI), A, a, $R^1$, $R^2$, $R^3$ and $R^6$ have the meanings already given above.

The imine of formula (XI) may be reacted either with at least one carboxylic acid and/or thiocarboxylic acid, preferably in the form of a carboxylic and/or thiocarboxylic acid chloride, ester or anhydride to form the corresponding amide and/or thioamide or it may be reacted with at least one carbonate and/or thiocarbonate, preferably in the form of a chloroformic acid and/or chlorothioformic acid ester to form the corresponding urethane and/or thiourethane, whereupon the resulting imine can ultimately be hydrogenated by suitable methods to form the amine of formula (I c).

For this reaction the same carboxylic acids and/or thiocarboxylic acids and carbonates and/or thiocarbonates are suitable as already mentioned for a reaction with an aldehyde Y3 of formula (VIII).

An imine of formula (XI) is obtained in particular by reacting at least one aldehyde Y3 of formula (VIII) with at least one suitable amine PA of formula (II) in a suitable ratio, but where amines PA having secondary amino groups are not suitable.

The amines of formula (I) are novel compounds with surprising properties. They are typically liquid at room temperature and have a low viscosity which is a major advantage for many applications. The term "low viscosity" is used here to refer to a viscosity of less than 3000 mPa·s, in particular less than 1500 mPa·s, measured with a cone-plate viscometer at 20° C. Nevertheless the amines of formula (I) have a low volatility and little odor, which is rarely the case for low-viscosity amines otherwise. In addition, they usually have such a low reactivity with $CO_2$ that—in contrast with many amines known in the state of the art—they do not form crusts or precipitates or undergo an increase in viscosity when exposed to air. This is a major advantage for many applications.

Another advantage is the simple accessibility of the amines of formula (I), namely they can be synthesized in high purity and high yield in a simple process that starts with commercially available primary amines and the aldehydes ALD of formula (III) described here and does not require any complex workup steps. This is possible because the formation of imine between the aldehyde ALD and the primary amino groups may also proceed spontaneously and without the formation of amine, even without active removal of water; hydrogenation is surprisingly easily accomplished—even at a relatively low hydrogen pressure and a relatively low temperature—despite the steric hindrance due to the tertiary substitution of the imino group—and the corresponding secondary imino groups of the amines of formula (I) do not participate in the alkylation reaction, so there cannot be any overalkylation with the loss of NH functionality.

The special structure of the amines of formula (I) permits a large number of advantageous applications. The use of amines of formula (I) as curing agents in curable compounds is especially advantageous, where in particular their compatibility with such compositions is surprisingly good. As a component of curable compounds, the amines of formula (I) yield excellent properties. On the one hand, self-leveling epoxy resin compositions can be formulated, requiring relatively little or no diluting additives, such as solvents, in particular benzyl alcohol and which have hardly any blushing tendency in curing and which yield polymer films of an excellent optical and mechanical quality. In addition, rapidly curing polyurethane and polyurea compositions with a high mechanical quality and excellent light stability can be obtained with these substances and have excellent processability because of the comparatively long pot life. Such rapidly curing compositions have the advantage that they can be reworked very early after application.

For use of the amines of formula (I), especially suitable curable compounds include those based on polyepoxies (epoxy resins) or polyisocyanates (polyurethanes and polyureas). Such curable compounds may be used, for example, as hard and soft foams, molded blocks, elastomers, fibers, fiber composite materials (composites), films or membranes, in particular as casting compounds, sealing substances and adhesives such as in particular electrical insulation compounds, spackling compounds, joint sealing compounds, mounting adhesives, automotive body adhesives, disk adhesives, sandwich element adhesives, half-shell adhesives, e.g., for rotor blades of wind power plants, laminating adhesives, laminate adhesives or anchoring adhesives; as well as in particular as coatings, covering, paints, enamels, seals, primers and foundations for construction and industrial applications such as, for example, floor coverings and floor coatings for interior rooms such as offices, industrial buildings, gymnasiums or refrigeration rooms or in the outdoor area for balconies, terraces, parking lots, bridges or roofs, protective coatings for concrete, cement, metals or plastics, for example, for surface sealing of loading surfaces, tanks, silos, shafts, pipelines or tubing lines, where these coatings protect the respective substrates in particular from corrosion, abrasion, moisture and/or chemicals; as well as for use as precoats, adhesive paints or for hydrophobization of surfaces.

The amines of formula (I) can thus be used to advantage in fiber-reinforced composite materials (composites), casting compounds, sealing materials, adhesives, coatings, paints, enamels, seals, foundations, primers, foams, molded blocks, elastomers, fibers, films and membranes.

Amines of formula (I) which have silane groups as a component of curable compounds may act not only as curing agents but also as crosslinking agents and/or as adhesion promoters and/or as accelerators and/or as desiccants, where silane-functional moisture-curing compounds are also suitable as curable compounds in particular. Furthermore, amines of formula (I) having silane groups may also be used as adhesion promoters between plastics and various substrates and for coating surfaces, for example, to improve their properties with respect to soiling tendency, ease of cleaning, etc. They may therefore be used as such or as an ingredient of solutions and compositions, for example, as free treatment agents or activators, as an undercoat or primer.

The amines of formula (I) are especially suitable on the one hand as ingredients of compositions based on epoxy resins, in particular for flat surface applications, for example, as floor coverings, coatings or paints. The amines of formula (I) are, as already mentioned, low viscosity substances having a low volatility and little odor which have special secondary amino groups. They are readily compatible with the usual commercial epoxy resins. Due to their use as curing agents, the primary amino group content of epoxy resin composition may be kept so low that hardly any reactions occur with $CO_2$ from the atmosphere. This therefore largely eliminates blushing effects in surface application even under unfavorable reaction conditions, i.e., conditions that promote blushing, namely at a low curing temperature, for example, in the range from 0 to 10° C. and in the presence of high atmospheric humidity. Due to the use of amines of formula (I) as curing agents, therefore epoxy resin compositions, which are largely or entirely free of the additives according to the state of the art that reduce blushing such as in particular benzyl alcohol and harden within a reasonable amount of time to form clear non-tacky films with an attractive surface and a good hardness, are now accessible.

Also especially suitable are the amines of formula (I) as ingredients of compositions containing isocyanate groups, in particular for polyurethane and polyurea coatings. In curing polyisocyanates with amines, the very high reactivity of the amino groups with isocyanate groups often leads to problems in processing. With the amines of formula (I), however, the polyurethane compositions and polyurea compositions that are obtained have a low viscosity, even with little or no solvent content, have hardly any odor and have a well-manageable reactivity, so that readily processable and rapidly curing coatings with a high light stability, good mechanical properties, good adhesion to a variety of substrates and excellent resistance are accessible. Amines of formula (I) with relatively large radicals $X^a$ to $X^d$ may also have an elastifying effect resembling that of plasticizers on the cured compound, such that they are bound into the polymer during curing, in contrast with the usual plasticizers, and therefore there are no migration-related problems such as bleeding, staining, substrate damage or the like. One large radical that may have such an elastifying effect is in particular the lauroyloxy radical.

The term "polyurethane" comprises all polymers synthesized according to the so-called diisocyanate polyaddition process. Thus polyurethanes usually contain urethane or thiourethane groups and in particular also urea groups. However, the term polyurethane also includes polymers which are almost or entirely free of urethane groups. In particular these include so-called polyureas, polyether polyureas and polyester polyureas as well as polyether polyurethanes, polyester polyurethanes, polyisocyanurates and polycarbodiimides.

For use in compositions containing isocyanate groups, especially suitable amines of formula (I) are those in which a stands for 2 or 3, in particular for 2, and in which A is free of primary and secondary amino groups. Such amines of formula (I) react comparatively slowly with isocyanate groups and have a good compatibility with polyurethane and polyurea compositions.

The amines of formula (I) may also be used for synthesis of adducts, where at least one amino group of an amine of formula (I) is reacted with at least one compound which can react with secondary or primary amino groups.

Another subject matter of the invention is an adduct AD from the reaction of at least one amine of formula (I) with at least one compound VB which has at least one, preferably at least two reactive groups RG where the reactive groups RG are selected from the group consisting of isocyanate, isothiocyanate, cyclocarbonate, epoxide, episulfide, aziridine, acryl, methacryl, 1-ethynylcarbonyl, 1-propinylcarbonyl, maleimide, citraconimide, vinyl, isopropenyl and allyl groups as well as substances with various of the reactive groups mentioned above. The preferred groups are isocyanate, epoxide, acryl, maleimide, vinyl, isopropenyl and allyl groups. The epoxy group and the isocyanate group are especially preferred as the reactive group RG.

At least one secondary or primary amino group of an amine of formula (I) reacts in an addition reaction with at least one reactive group RG of compound VB to form an adduct AD.

The reaction may either be performed in such a way that the amino groups of the amine of formula (I) are present in a stoichiometric excess with respect to the reactive groups RG of the compound VB, such that the adducts AD having at least one, preferably at least two amino groups of formula (XII) can be obtained.

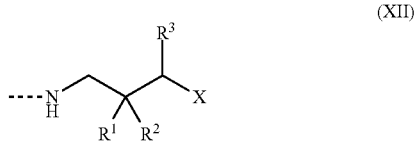

(XII)

$R^1$, $R^2$, $R^3$ and X in formula (XII) have the meanings already described above.

However, the reaction may also be performed in such a way that the reactive groups RG of the compound VB are present in a stoichiometric excess with respect to the primary and secondary amino groups of the amine of formula (I). In this way adducts AD having at least one, preferably at least two, reactive groups RG can be obtained, as already described above.

The reaction between the amine of formula (I) and the compound VB to form an adduct AD takes place under known reaction conditions such as those typically used for reactions between the reactive groups RG involved in the respective reaction. The reaction takes place using a solvent or preferably in the absence of solvents. Additives such as catalysts, initiators or stabilizers may optionally also be used. The reaction with isocyanate groups is preferably performed at room temperature, while the reaction with epoxy groups is preferably performed at an elevated temperature, for example, at 40° C. to 100° C.

Examples of suitable compound VB include:
monomeric and oligomeric polyisocyanates as well as reaction products of polyisocyanates with polyols having more than one isocyanate group, as mentioned below for synthesis of the adducts AD1 and AD2;
polyepoxies such as bis-(2,3-epoxycyclopentyl)ether, polyglycidyl ethers of polyvalent aliphatic and cycloaliphatic alcohols such as 1,4-butanediol, polypropylene glycols and 2,2-bis-(4-hydroxycyclohexyl)propane; polyglycidyl ethers of polyvalent phenols such as resorcinol, bis-(4-hydroxyphenyl)methane (bisphenol F), 2,2-bis-(4-hydroxyphenyl)propane (bisphenol A), 2,2-bis-(4-hydroxy-3,5-dibromophenyl)propane, 1,1,2,2-tetrakis-(4-hydroxyphenyl)ethane, condensation products of phenols with formaldehyde obtained under acidic conditions such as phenol novolacs and cresol novolacs as well as polyglycidyl ethers prelengthened with these alcohols and phenols or with polycarboxylic acids such as, for example, dimeric fatty acids or with a mixture thereof; polyglycidyl esters of polyvalent carboxylic acids such as phthalic acid, terephthalic acid, tetrahydrophthalic acid and hexahydro phthalic acid; N-glycidyl derivatives of amities, amides and heterocyclic nitrogen bases such as N,N-diglycidyl aniline, N,N-diglycidyl toluidine, N,N,O-triglycidyl-4-aminophenol, N,N,N',N'-tetraglycidyl-bis-(4-aminophenyl)methane, triglycidyl cyanurate and triglycidyl isocyanurate;
compounds having more than one acryl, methaeryl or acrylamide group such as tris-(2-hydroxyethyl)isocyanurate tri(meth)acrylate, tris-(2-hydroxyethyl) cyanurate tri (meth)acrylate, N,N',N"-tris-(meth)acryloyl perhydrotriazine; acrylates and methacrylates of aliphatic polyethers, polyesters, novolacs, phenols, aliphatic or cycloaliphatic alcohols, glycols and polyester glycols as well as mono- and polyalkoxylated derivatives of the compounds mentioned above, for example, ethylene glycol di(meth)acrylate, tetraethylene glycol di(meth)acrylate, tripropylene glycol di(meth)acrylate, polyethylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, trimethylolpropane tri(meth)acrylate, pentaerythritol tetra(meth)acrylate, dipentaerythritol tetra (meth)acrylate, dipentaerythritol penta(meth)acrylate, dipentaerythritol hexa(meth)acrylate; acryl- or methacryl-functional polybutadienes, polyisoprenes or block copolymers thereof; adducts of polyepoxies such as the epoxies mentioned above with acrylic and methacrylic acid; polyurethane(meth)acrylates; acrylamides such as N,N'-methylene bisacrylamide;
compounds having more than one 1-ethynylcarbonyl or 1-propinylcarbonyl group;
compounds having more than one maleimide or citraconimide group;
compounds having more than one vinyl and/or isopropenyl group;

compounds having more than one allyl group;
as well as heterofunctional compounds, i.e., having at least two different ones of the reactive groups mentioned above.

Especially suitable examples of compounds VB include, on the one hand, monomeric and oligomeric polyisocyanates as well as reaction products of polyisocyanates with polyols having more than one isocyanate group and, on the other hand, polyepoxies.

The adducts AD are suitable for the same uses as the amines of formula (I).

In particular adducts AD which have amino groups of formula (XII) are suitable for the same applications as the amines of formula (I) in particular as curing agents in curable compounds. Likewise, however, such adducts AD which have the reactive groups RG described above are also suitable as ingredients of curable compounds.

Adducts AD having silane groups are additionally suitable for the same uses as the amines of formula (I) which have silane groups.

Of the adducts AD described above, those of particular interest are the adducts having at least two amino groups of formula (XII) in one embodiment, hereinafter referred to as adducts AD1. Preferred adducts AD1 are derived from polyisocyanates as compound VB.

Of the adducts AD described above, adducts AD2 which have at least two isocyanate groups and were synthesized using a polyisocyanate as compound VB are of particular interest in another embodiment.

In particular mono- and/or oligomeric aliphatic, cycloaliphatic, araliphatic or aromatic polyisocyanates are suitable as the polyisocyanate for synthesis of the adducts AD2 and the preferred adducts AD1, these polyisocyanates including 1,4-tetramethylene diisocyanate, 1,6-hexamethylene diisocyanate (HDI), 2-methylpentamethylene 1,5-diisocyanate, 2,2,4- and 2,4,4-trimethyl-1,6-hexamethylene diisocyanate (TMDI), 1,10-decamethylene diisocyanate, 1,12-dodecamethylenediisocyanate, lysine and lysine ester diisocyanate, cyclohexane 1,3- and 1,4-diisocyanate and any mixtures of these isomers, 1-methyl-2,4- and -2,6-diisocyanatocyclohexane and any mixtures of these isomers (HTDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl)cyclohexane, m- and p-xylylene diisocyanate (m- and p-XDI), 1,3,5-tris-(isocyanatomethyl)benzene, m- and p-tetramethyl 1,3- and 1,4-xylylene diisocyanate (m- and p-TMXDI), bis-(1-isocyanato-1-methylethyl) naphthalene, dimeric and trimeric fatty acid isocyanates such as 3,6-bis-(9-isocyanatononyl)-4,5-di-(1-heptenyl)cyclohexene (dimeryl diisocyanate), α,α,α',α',α",α"-hexamethyl-1,3,5-mesitylene triisocyanate, 2,4- and 2,6-toluoylene diisocyanate and any mixtures of these isomers (TDI), 4,4'-, 2,4'- and 2,2'-diphenyl methane diisocyanate and any mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tris-(4-isocyanatophenyl) methane, tris-(4-isocyanato-phenyl)thiophosphate; oligomers of these isocyanates containing uretdione, isocyanurate or iminooxadiazine dione group; modified polyisocyanates containing ester, urea, urethane, biuret, allophanate, carbodiimide, uretonimine or oxadiazine trione groups as well as polyurethane polymers that contain isocyanate groups, i.e., the reaction products of polyisocyanates with substances having two or more hydroxyl groups (so-called "polyols") containing more than one isocyanate group such as divalent alcohols or those having a higher valence, glycols or amino alcohols, polyhydroxy-functional polyethers, polyesters, polyacrylates, polycarbonates or polyhydrocarbons, in particular polyethers.

The adducts AD1 are suitable in particular as curing agents in compositions containing isocyanate groups. They have a viscosity that makes them easy to handle. This is not self-evident, in particular in the case of adducts based on polyisocyanates as compound VB. In other words, when amines known from the state of the art are adducted in the manner described here, numerous problems may occur. In the case of amines containing mainly primary amino groups, the reactivity with polyisocyanates is usually so high that the reaction proceeds in an uncontrolled manner and very high viscosities or even solids may be obtained despite the fact that the stoichiometric ratio is suitable per se. However, even in the case of relatively slow secondary amines, it is often difficult to obtain adducts with a viscosity that is easy to handle. The comparatively low viscosity of the adducts AD1 may be attributed to the radicals $X^a$ to $X^d$ which originate from the aldehyde ALD and are bound to the substituents of the urea groups thus formed in that these adducts function as a type of internal solvent. The adducts AD1 as the curing agent are very compatible with compositions containing isocyanate groups. Such compositions have a comparatively long processing time, which is in a range similar to that of the compositions with the corresponding amines of formula (I) as the curing agent. Due to the use of adducts AD1 this also results in the possibility of increasing the amount by volume and weight of the curing agent in the composition, which could be highly desirable in the case of a two-component application in order to achieve the desired mixing ratio between the two components. In addition, the curing of such compositions to form a plastic is even faster when an adduct AD1 is used as the curing agent instead of an amine of formula (I) because some of the reactions required for the curing have already taken place during the synthesis of the adduct. Therefore such a composition can be reprocessed even sooner after application.

The adducts AD2 are suitable in particular as the polyisocyanate for formulation of polyurethane and polyurea coatings. They have the great advantage that their isocyanate groups are stable in storage in the presence of the urea groups derived from the adducting in the exclusion of moisture, which is often not the case when using amines from the state of the art for adducting. The adducts AD2, in particular those derived from amines of formula (I b) containing ester groups also have a comparatively low viscosity, which makes their use in formulating polyurethane and polyurea coatings especially attractive. Use of the adducts AD2 in polyurethane and polyurea compositions also has the advantage that in this way an amine of formula (I) in a completely reacted form is used as an ingredient of the curable compound, which in turn results in a very rapid curing and greatly facilitates the establishment of the desired mixing ratio of a two-component composition.

Amines of formula (I) containing primary amino groups may be reacted with Michael acceptors such as maleic acid diesters, fumaric acid diesters, citraconic acid diesters, acrylic acid esters, methacrylic acid esters, cinnamic acid esters, itaconic acid diesters, vinyl phosphonic acid diesters, vinyl sulfonic acid aryl esters, vinyl sulfones, vinyl nitriles, 1-nitroethylenes or Knoevenagel condensation products such as, for example, those from malonic acid diesters and aldehydes such as formaldehyde, acetaldehyde or benzaldehyde wherein the resulting reaction products have a reduced primary amino group content or they are entirely free of primary amino groups. Thus, for example, it is conceivable to react a primary aliphatic diamine with a substoichiometric amount of aldehyde ALD in a reductive alkylation process like that described above and to next react the remaining primary amino groups partially or completely with any one of the Michael acceptors mentioned above.

Another subject of the invention is curable compound containing either at least one amine of formula (I) or at least one adduct AD. Such a curable compound preferably has epoxy groups and/or isocyanate groups.

Another subject of the invention is a curable compound in the form of a composition Z1, which has isocyanate groups and contains
- a) at least one polyisocyanate and
- b) at least one curing agent compound HV which has at least two reactive groups selected from the group consisting of primary amino groups, secondary amino groups, hydroxyl groups and mercapto groups;

with the provision that the polyisocyanate and/or the curing agent compound HV is a compound selected from the group consisting of the amines of formula (I), the adducts AD1 and the adducts AD2.

The term "polyisocyanate" includes compound having two or more isocyanate groups regardless of whether they are monomeric di- or triisocyanates, oligomeric diisocyanates or adducts and polymers containing isocyanate groups.

In one embodiment of the invention a suitable polyisocyanate is an adduct AD2 which has at least two isocyanate groups as described above.

In another embodiment, a polyurethane polymer PUP containing isocyanate groups is suitable as the polyisocyanate.

A suitable polyurethane polymer PUP is obtainable in particular from the reaction of at least one polyol with at least one polyisocyanate. This reaction may take place by reacting the polyol and the polyisocyanate by the usual methods, for example, at temperatures of 50° C. to 100° C., optionally also with the use of suitable catalysts, such that the polyisocyanate is dosed in such a way that its isocyanate groups are present in a stoichiometric excess in relation to the hydroxyl groups of the polyol. The polyisocyanate is advantageously dosed in such a way as to maintain an NCO/OH ratio of 1.3:25 in particular 1.5:15. The "NCO/OH ratio" is understood to be the ratio of the number of isocyanate groups used to the number of hydroxyl groups used. After the reaction of all the hydroxyl groups of the polyol, a free isocyanate group content of 0.5% by weight to 30% by weight, especially preferably from 0.5 to 25% by weight preferably remains in the polyurethane polymer PUP.

The polyurethane polymer PUP can optionally be synthesized with the joint use of plasticizers, where the plasticizers used do not contain any groups that are reacted with isocyanates.

In particular the following commercial polyols or mixtures thereof may be used for synthesis of a polyurethane polymer PUP:

It is also possible to use polyoxy alkylene polyols, also known as polyether polyols or oligoetherols, which are polymerization products of ethylene oxide, 1,2-propylene oxide, 1,2- or 2,3-butylene oxide, oxetan, tetrahydrofuran or mixtures thereof, optionally polymerized with the help of an initiator molecule with two or more active hydrogen atoms such as, for example, water, ammonia or compounds having several OH or NH groups such as, for example, 1,2-ethanediol, 1,2- and 1,3-propanediol, neopentyl glycol, diethylene glycol, triethylene glycol, the isomeric dipropylene glycols and tripropylene glycols, the isomeric butane diols, pentane diols, hexane diols, heptane diols, octane diols, nonane diols, decane diols, undecane diols, 1,3- and 1,4-cyclohexane dimethanol, bisphenol A, hydrogenated bisphenol A, 1,1,1-trimethylol ethane, 1,1,1-trimethylolpropane, glycerol, aniline as well as mixtures of the compounds mentioned above. Both polyoxy alkylene polyols having a low degree of unsaturation (measured according to ASTM D-2849-69 and given in milliequivalents of unsaturation (gram of polyol (mEq/g)) synthesized, for example, with the help of so-called double metal cyanide complex catalysts (DMC catalysts) as well as polyoxy alkylene polyols with a higher degree of unsaturation synthesized, for example, with the help of anionic catalysts such as NaOH, KOH, CsOH or alkali alcoholates. Polyoxy alkylene diols or polyoxy alkylene triols are especially suitable, in particular polyoxy ethylene and polyoxy propylene di- and triols. Polyoxy alklylene diols and triols with a degree of unsaturation of less than 0.02 mEq/g and with a molecular weight in the range of 1000 to 30,000 g/mol as well as polyoxy propylene diols and triols with a molecular weight of 400-8000 g/mol are especially suitable. So-called ethylene oxide-terminated (EO end-capped, ethylene oxide end-capped) polyoxy propylene polyols are also especially suitable. The latter are special polyoxy propylene polyols which are obtained, for example, by further alkoxylating pure polyoxy propylene polyols, in particular polyoxy propylene diols and triols with ethylene oxide after the end of the polypropoxylation reaction and therefore they have primary hydroxyl groups.

Styrene-acrylonitrile- or acrylonitrile-methyl methacrylate-grafted polyether polyols.

Polyester polyols, also known as oligoesterols, synthesized by known methods in particular, the polycondensation of hydroxycarboxylic acids or the polycondensation of aliphatic and/or aromatic polycarboxylic acids with divalent or polyvalent alcohols.

Especially suitable polyester polyols are those synthesized from divalent to trivalent in particular divalent alcohols such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimeric fatty acid diol (dimer diol), hydroxypivalic acid neopentyl glycol ester, glycerol, 1,1,1-trimethylolpropane or mixtures of the alcohols mentioned above with organic di- or tricarboxylic acids in particular dicarboxylic acids or their anhydrides or esters such as, for example, succinic acid, glutaric acid, adipic acid, trimethyladipic acid, suberic acid, azelaic acid, sebacic acid, dodecane dicarboxylic acid, maleic acid, fumaric acid, dimer fatty acid, phthalic acid, phthalic acid anhydride, isophthalic acid, terephthalic acid, dimethyl terephthalate, hexahydro phthalic acid, trimellitic acid and trimellitic acid anhydride or mixtures of the acids mentioned above as well as polyester polyols from lactones such as, for example, from ε-caprolactone and initiators such as the divalent or trivalent alcohols mentioned above.

Especially suitable polyester polyols are polyester diols.

Polycarbonate polyols such as those accessible by reacting, for example, the alcohols mentioned above (which are used for synthesis of the polyester polyols) with dialkyl carbonates, diaryl carbonates or phosgene.

Blocked copolymers which have at least two hydroxyl groups and have at least two different blocks with a polyether, a polyester and/or polycarbonate structure of the type described above, in particular polyether polyester polyols.

Polyacrylate and polymethacrylate polyols.

Polyhydroxy-functional fats and oils, for example, natural fats and oils in particular castor oil; or so-called oleochemical polyols obtained by chemical modification of natural fats and oils, for example, the epoxy polyesters and/or epoxy polyethers obtained by epoxidation of unsaturated oils and subsequent ring opening with carboxylic acids and/or alcohols, or polyols obtained by hydroformylation and hydrogenation of unsaturated oils; or polyols obtained from natural fats and oils by degradation processes such as alcoholysis or ozonolysis and subsequent chemical linkage, for example, by transesterification or dimerization of the resulting degradation products or derivatives thereof. Suitable degradation products of natural fats and oils include in particular fatty acid and fatty alcohols as well as fatty acid esters, in particular the methyl esters (FAME), which can be derivatized by hydroformylation and hydrogenation, for example, to form hydroxy fatty acid esters.

Polyhydrocarbon polyols, also known as oligohydrocarbonols such as, for example, polyhydroxy-functional polyolefins, polyisobutylenes, polyisoprenes; polyhydroxy-functional ethylene-propylene, ethylene-butylene or ethylene-propylene diene copolymers such as those synthesized, for example, by the company Kraton Polymers; polyhydroxy-functional polymers of dienes in particular 1,3-butadiene which may also be synthesized in particular from anionic polymerization; polyhydroxy-functional copolymers of dienes, such as 1,3-butadiene or diene mixtures and vinyl monomers such as styrene, acrylonitrile, vinyl chloride, vinyl acetate, vinyl alcohol, isobutylene and isoprene, for example, polyhydroxy-functional acrylonitrile butadiene copolymers, such as those that can be synthesized from epoxies or amino alcohols and carboxy-terminated acrylonitrile-butadiene copolymers (for example, commercially available under the names Hypro® (previously Hycar®) CTBN and CTBNX and ETBN by Nanoresins AG, Germany and/or Emerald Performance Materials LLC; as well as hydrogenated polyhydroxy-functional polymers or copolymers of dienes.

The polyols mentioned above preferably have an average molecular weight of 250-30,000 g/mol, in particular 400-20,000 g/mol and they preferably have an average OH functionality in the range of 1.6 to 3.

Preferred polyols include polyether, polyester, polycarbonate and polyacrylate polyols preferably di- and triols. Polyether polyols in particular polyoxy propylene and polyoxy propylene-polyoxyethylene polyols as well as liquid polyester polyols and polyether polyester polyols are especially preferred.

In addition to the polyols mentioned above, small amounts of low-molecular divalent or polyvalent polyols such as, for example, 1,2-ethanediol, 1,2- and 1,3-propanediol, neopentyl glycol, diethylene glycol, triethylene glycol, the isomeric dipropylene glycol and tripropylene glycol, the isomeric butane diols, pentane diols, hexane diols, heptane diols, octane diols, nonane diols, decane diols, undecane diols, 1,3- and 1,4-cyclohexanedimethanol, hydrogenated bisphenol A, dimeric fatty alcohols, 1,1,1-trimethylolethane, 1,1,1-trimethylolpropane, glycerol, pentaerythritol, sugar alcohols such as xylitol, sorbitol or mannitol, sugars such as sucrose, other higher valency alcohols, low-molecular alkoxylation products of the divalent and polyvalent alcohols mentioned above and mixtures of the alcohols mentioned above may also be used in the synthesis of the polyurethane polymer PUP. Small amounts of polyols with an average OH functionality of more than 3 may also be used, for example, sugar polyols.

Aromatic or aliphatic polyisocyanates in particular the diisocyanates are used as the polyisocyanate for the synthesis of a polyurethane polymer PUP having isocyanate groups.

Suitable aromatic polyisocyanate include in particular monomeric di- or triisocyanates such as 2,4- and 2,6-toluoylene diisocyanate and any mixtures of these isomers (TDI), 4,4'-, 2,4'- and 2,2'-diphenyl methane diisocyanate and any mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tris-(4-isocyanatophenyl)methane, tris-(4-isocyanatophenyl)thiophosphate as well as any mixtures of the isocyanates mentioned above. MDI and TDI are preferred. In the case of MDI, 2,4'-diphenylmethane diisocyanate is also preferred in particular.

Suitable aliphatic polyisocyanates include in particular monomeric di- or triisocyanates such as 1,4-tetramethylenediisocyanate, 2-methylpentamethylene 1,5-diisocyanate, 1,6-hexamethylendiisocyanate (HDI), 2,2,4- and 2,4,4-trimethyl 1,6-hexamethylene diisocyanate (TMDI), 1,10-decamethylendiisocyanate, 1,12-dodecamethylene diisocyanate, lysine and lysine ester diisocyanate, cyclohexane 1,3- and 1,4-diisocyanate, 1-methyl-2,4- and -2,6-diisocyanato cyclohexane and any mixtures of these isomers (HTDI or $H_6$TDI), 1-isocyanato-3,3,5-trimethyl-5-isocyanatomethylcyclohexane isophorone diisocyanate or IPDI), perhydro-2,4'- and -4,4'-diphenylmethane diisocyanate (HMDI or $H_{12}$MDI), 1,4-diisocyanato 2,2,6-trimethylcyclohexane (TMCDI), 1,3- and 1,4-bis-(isocyanatomethyl)cyclohexane, m- and p-xylylene diisocyanate (m- and p-XDI), m- and p-tetramethyl-1,3- and -1,4-xylylene diisocyanate (m- and p-TMXDI), 1,3,5-tris-(isocyanatomethyl)benzene, bis-(1-isocyanato-1-methylethyl) naphthalene, dimeric and trimeric fatty acid isocyanates such as 3,6-bis-(9-isocyanatononyl)-4,5-di-(1-heptenyl)-cyclohexene (dimeryl diisocyanate), $\alpha,\alpha,\alpha',\alpha',\alpha''$, $\alpha''$-hexamethyl-1,3,5-mesitylene triisocyanate as well as any mixtures of the isocyanates mentioned above. HDI and IPDI are preferred.

In another embodiment, a polyisocyanate PI in the form of a monomeric di- or triisocyanate or an oligomer of a monomeric diisocyanate or a derivative of a monomeric diisocyanate is suitable as the polyisocyanate, in particular the aromatic and aliphatic di- and triisocyanates mentioned above being suitable as the monomeric di- or triisocyanate.

Especially suitable as the polyisocyanate PI are the oligomers or derivatives of monomeric diisocyanates in particular HDI, IPDI, TDI and MDI. Commercially available types include in particular HDI biurets, for example, as Desmodur® N 100 and N 3200 (from Bayer), Tolonate® HDB and HDB-LV (from Rhodia) and Duranate® 24A-100 (from Asahi Kasei); HDI isocyanurates, for example, as Desmodur® N 3300, N 3600 and N 3790 BA (all of these are from Bayer), Tolonate® HDT, HDT-LV and HDT-LV2 (from Rhodia), Duranate® TPA-100 and THA-100 (from Asahi Kasei) and Coronate® HX (from Nippon Polyurethane); HDI uretdiones, for example, as Desmodur® N 3400 (from Bayer); HDI iminooxadiazine diones, for example, as Desmodur® XP 2410 (from Bayer); HDI allophanates, for example, as Desmodur® VP LS 2102 (from Bayer); IPDI isocyanurates, for example, in solution as Desmodur® Z 4470 (from Bayer) or in solid form as Vestanat® T1890/100

(from Degussa); TDI oligomers, for example, as Desmodur® IL (from Bayer); as well as mixed isocyanurates based on TDI/HDI, for example, as Desmodur® HL (from Bayer). In addition, forms of MDI that are liquid at room temperature (so-called "modified MDI") are especially suitable; these are mixtures of MDI and MDI derivatives such as, for example, MDI carbodiimides and/or MDI uretonimines or MDI urethanes, which are known, for example, under brand names such as Desmodur® CD, Desmodur® PF, Desmodur® PC (all from Bayer) and Isonate® 143L (from Dow) as well as mixtures of MDI and MDI homologs (polymeric MDI or PMDI), available under brand names such as Desmodur® VL, Desmodur® VL50, Desmodur® VL R10, Desmodur® VL R20 and Desmodur® VKS 20F (all from Bayer), Isonate® M 309, Voranate® M® 229 and Voranate® M 580 (all from Dow) or Lupranate® M 10 R (from BASF).

In practice, the oligomeric polyisocyanates PI mentioned above are usually mixtures of substances with different degrees of oligomerization and/or chemical structures. They preferably have an average NCO functionality of 2.1 to 4.0 and contain in particular isocyanurate, imino oxadiazine dione, uretdione, urethane, biuret, allophanate, carbodiimide, uretonimine or oxadiazine trione groups.

Forms of MDI that are liquid at room temperature are preferred as the polyisocyanate PT, as well as the oligomers of HDI, IPDI and TDI, in particular the isocyanurates and the biurets.

Also suitable as the polyisocyanate are mixtures of at least one adduct AD2 and/or at least one polyurethane polymer PUP and/or at least one polyisocyanate PI as described above.

So-called quasi-prepolymers are suitable in particular as the polyisocyanate. These are either a polyurethane polymer PUP for the synthesis of which at least one polyol is reacted with a relatively great excess of at least one monomeric diisocyanate; or it is the reaction product of at least one polyamine with a relatively great excess of at least one monomeric diisocyanate. Suitable polyamines for this purpose include in particular polyoxy alkylene diamines and polyoxy alkylene triamines.

Such quasi-prepolymers are commercially available, for example, as Suprasec® 1007, Suprasec® 2008, Suprasec® 2021, Suprasec® 2029, Suprasec® 2054, Suprasec® 2058, Suprasec® 2067, Suprasec® 2234, Suprasec® 2444, Suprasec® 2445, Suprasec® 2783, Suprasec® 2980, Suprasec® 2982, Suprasec® 9603, Suprasec® 9608, Suprasec® 9616, Rubinate® 1209, Rubinate® 1790, Rubinate® 9009, Rubinate'19271, Rubinate® 9447, Rubinate® 9480 and Rubinate® 9495 (from Huntsman) or as Desmodur® E 23, Desmodur® E 210 and Desmodur® E 743 (from Bayer) or as Echelon® MP 100, Echelon® MP 101, Echelon® MP 102, Echelon® MP 104, Echelon® MP 106, Echelon® MP 107, Echelon® MP 108 and Echelon® MC 400 (from Dow) or as Lupranate® 279, Lupranate® 5060 and Lupranate® 5080 (from BASF).

Quasi-prepolymers based on MDI preferably have an increased amount of 2,4'-MDI. Such quasi-prepolymers are characterized by a lower reactivity as such, based on primarily 4,4'-MDI.

The polyisocyanate may in particular also be a mixture of at least one polyisocyanate PI and at least one adduct AD2.

In one embodiment, the amines of formula (I) described above are suitable as the curing agent compound HV. Amines of formula (I) in which a stands for 2 or 3, in particular for 2, and in which A is free of primary and secondary amino groups are preferred.

In another embodiment, the adducts AD1 described above are suitable as the curing agent compound HV. Preferred adducts AD1 are derived from at least one polyisocyanate as compound VB.

In addition, polyamines and amino alcohols, in particular the following are suitable as the curing agent compound HV:
the amines PA of formula (II) described above if they have at least two groups that are reactive with isocyanate groups;
secondary aliphatic polyamines such as in particular N,N-dibutyl ethylene diamine, N,N'-di-tert-butyl ethylene diamine, N,N-diethyl-1,6-hexane diamine, 1-(1-methylethylamino)-3-(1-methylethyl amino methyl)-3,5,5-trimethyl cyclohexane (Jefflink® 754 from Huntsman), $N^4$-cyclohexyl-2-methyl-$N^2$-(2-methyl propyl)-2,4-pentane diamine, N,N'-dialkyl-1,3-xylylene diamine, bis-(4-(N-alkylamino)cyclohexyl) methane, N-alkylated polyether amines, for example, Jeffamine® grades SD-231, SD-401, ST-404 and SD-2001 (from Huntsman), products from the addition reaction of primary aliphatic polyamines with Michael acceptors in a reaction like a Michael reaction, such as maleic acid diester, fumaric acid diester, citraconic acid diester, acrylic acid ester, methacrylic acid ester, cinnamic acid ester, itaconic acid diester, vinyl phosphonic acid diester, vinyl sulfonic acid aryl ester, vinyl sulfones, vinyl nitriles, 1-nitroethylenes or Knoevenagel condensation products such as, for example, those from malonic acid diesters and aldehydes such as formaldehyde, acetaldehyde or benzaldehyde as well as commercial secondary aliphatic polyamines such as Gaskamine® 240 (from Mitsubishi) or the Desmophen® grades NH 1220, NH 1420 and NH 1520 (from Bayer);
primary and/or secondary aromatic polyamines such as in particular m- and p-phenylene diamine, 4,4'-,2,4' and 2,2'-diaminodiphenylmethane, 3,3'-dichloro-4,4'-diaminodiphenylmethane (MOCA), 2,4- and 2,6-toluoylene diamine, mixtures of 3,5-dimethylthio-2,4- and -2,6-toluoylene diamine (obtainable as Ethacure® 300 from Albemarle), mixtures of 3,5-diethyl-2,4- and -2,6-toluoylene diamine (DETDA), 3,3',5,5'-tetraethyl-4,4'-diaminodiphenyl methane (M-DEA), 3,3',5,5'-tetraethyl-2,2'-dichloro-4,4'-diaminodiphenyl methane (M-CDEA), 3,3'-diisopropyl-5,5'-dimethyl-4,4'-diaminodiphenyl methane (M-MIPA), 3,3',5,5'-tetraisopropyl-4,4'-diaminodiphenyl methane (M-DIPA), 4,4'-diamino diphenylsulfone (DDS), 4-amino-N-(4-aminophenyl)benzene sulfonamide, 5,5'-methylenedianthranilic acid, dimethyl-(5,5'-methylene dianthranilate), 1,3-propylene-bis-(4-aminobenzoate), 1,4-butylene-bis-(4-aminobenzoate), polytetramethylene oxide-bis-(4-aminobenzoate) (obtainable as Versalink® from Air Products), 1,2-bis-(2-aminophenylthio)ethane, N,N'-dialkyl-p-phenylene diamine such as, for example, Unilink® 4100 (from UOP), diphenyl methane such as, for example, Unilink® 4200 (from UOP), 2-methylpropyl-(4-chloro-3,5-diamino benzoate) and tert-butyl-(4-chloro-3,5-diamino benzoate);
amino alcohols such as in particular diethanol amine, diisopropanol amine, 3-methylamino-1,2-propanediol, 2-(methylamino) ethanol, 2-(ethylamino) ethanol, 2-(butylamino) ethanol, 2-(cyclohexylamino) ethanol, 3-pyrrolidinol, 3- or 4-hydroxypiperidine, 2-piperidinethanol, 2-[2-(1-piperazyl)]ethanol, 2-[2-(1-piperazyl) ethoxy]ethanol and N-hydroxyethylaniline.

Commercial polyols, in particular the polyols mentioned above for synthesis of the polyurethane polymers PUP described here are also suitable as the curing agent compound HV, in addition to molecular divalent or polyvalent alcohols and/or molecular alkoxylation products of these alcohols.

In addition, polythiols, in particular the compounds having mercaptan groups as mentioned below as possible ingredients of an epoxy resin composition Z2 are also suitable as the curing agent compound HV.

The composition Z1 containing isocyanate groups preferably comprises at least one polyoxy alkylene compound, especially preferably at least one polyoxy propylene compound, either in the form of a polyoxy alkylene diamine or polyoxy alkylene triamine—optionally in the form of an amine of formula (I)—or in the form of a polyoxy alkylene diol or a polyoxy alkylene triol or in the form of a polyisocyanate P, which is a reaction product of one of the polyoxy alkylene compounds mentioned above and a polyisocyanate. When fully cured, such compositions Z1 have an especially great ductility and elasticity.

The composition Z1 containing isocyanate groups preferably contains at least one compound which has a functionality of >2 with respect to isocyanate groups, primary amino groups, secondary amino groups, hydroxyl groups or mercapto groups, i.e., it contains more than two of the reactive groups mentioned above. Possible compounds with a functionality of >2 include an adduct AD2, a polyisocyanate P or a curing agent compound HV, in particular a triamine or a triol.

The average functionality of the first component containing isocyanate groups in a two-component composition Z1 is preferably in the range of 1.9 to 3.0, especially preferably in the range of 2.0 to 2.5.

The average functionality of the second isocyanate group-free component of a two-component composition Z1 is preferably in the range of 1.9 to 3.0, especially preferably in the range of 2.0 to 2.5.

One of the two components of a two-component composition Z1 preferably has a functionality of approximately 2.

The composition Z1 containing isocyanate groups may optionally contain at least one catalyst. Suitable catalysts include on the one hand nitrogen-containing compound, in particular tertiary amines and amidines such as in particular N-ethyl-diisopropyl amine, N,N,N',N'-tetramethylalkylene diamine, bis-(N,N-diethylamino ethyl) adipate, N,N,N-tris-(3-dimethylaminopropyl)amine, 1,4-diazabicyclo[2.2.2]octane (DABCO), 1,8-diazabicyclo[5.4.0]undec-7-ene (DBU), 1,5-diazabicyclo[4.3.0]non-5-ene (DBN), N-alkyl morpholines such as N-methylmorpholine and N-ethylmorpholine, N,N'-dimethyl piperazine, benzyldimethyl amine, N,N-dimethylcyclohexyl amine, N,N,N',N'',N'''-pentamethyl diethyl ene triamine, N,N,N',N'',N'''-pentamethyldipropylene triamine, N-(3-dimethyl aminopropyl)-N,N-diisopropanol amine, N'-(3-(dimethylamino)propyl)-N,N-dimethyl-1,3-propane diamine, 1-methyl-4(2-dimethylamino ethyl)piperazine, 1,3,5-tris-(3-(dimethylamino)propyl)hexahydro-s-triazine; nitrogen aromatic compounds, such as in particular 4-dimethyl aminopyridine, N-methyl imidazole, N-vinylimidazole or 1,2-dimethylimidazole; organic ammonium compounds or alkoxylated tertiary amines.

Also suitable as a catalyst are metal compounds, in particular tin compounds such as in particular dibutyl tin dichloride, dibutyl tin oxide, dibutyl tin diacetate, dibutyl tin dilaurate, dibutyl tin diacetyl acetonate, additional dibutyl tin dicarboxylates, dioctyl tin dicarboxylates such as in particular dioctyl tin dilaurate, monobutyl tin trichloride, tin(II) octoate and alkyl tin thioesters; bismuth compounds such as bismuth trioctoate and bismuth tris(neodecanoate); as well as compounds of zinc, manganese, iron, chromium, cobalt, copper, nickel, molybdenum, lead, cadmium, mercury, antimony, vanadium, titanium, zirconium or potassium.

Also suitable as catalysts are combinations of the compounds mentioned above in particular metal compounds and nitrogen compounds.

The compositions Z1 containing the isocyanate groups may optionally also contain other components, in particular the additives and auxiliary substances generally used in polyurethane compositions, for example, the following:

plasticizers, in particular carboxylic acid esters such as phthalates, in particular dioctyl phthalate, diisononyl phthalate or diisodecyl phthalate, adipates in particular dioctyl adipate, azelates and sebacates, organic phosphonic and sulfonic acid esters or polybutenes;

reactive diluents and crosslinking agents, for example, natural resins, fats or oils such as colophony, shellac, linseed oil, castor oil and soybean oil as well as latent curing agents such as aldimines, ketimines, enamines and oxazolidines derived from polyamines;

nonreactive thermoplastic polymers such as, for example, homo- or copolymers of unsaturated monomers in particular from the group comprising ethylene, propylene, butylene, isobutylene, isoprene, vinyl acetate and alkyl (meth)acrylates, in particular polyethylenes (PE), polypropylenes (PP), polyisobutylenes, ethylene vinyl acetate copolymers (EVA) and atactic poly-α-olefins (APAO);

solvents such as, for example, ketones such as acetone, methyl ethyl ketone, diisobutyl ketone, acetyl acetone, mesityl oxide, cyclohexanone, methyl cyclohexanone, acetates such as ethyl acetate, propyl acetate, butyl acetate, formates, propionates and malonates such as diethylmalonate; ethers such as dialkyl ether, ketone ether and ester ether, for example, diisopropyl ether, diethyl ether, dibutyl ether, diethylene glycol diethyl ether and ethylene glycol diethyl ether; aliphatic and aromatic hydrocarbons such as toluene, xylene, diisopropylnaphthalene, heptane, octane and petroleum fractions such as naphtha, white spirit, petroleum ether and gasoline, for example Solvesso® grades (from Exxon), halogenated hydrocarbons such as methylene chloride and n-alkylated lactams such as, for example N-methylpyrrolidone;

inorganic and organic fillers in particular ground or precipitated calcium carbonates which are optionally coated with fatty acids in particular stearates, barite (heavy spar), talc, quartz powders, quartz sand, dolomites, wollastonites, kaolins, calcinated kaolins, mica (potassium aluminum silicate), molecular sieves, aluminum oxides, aluminum hydroxides, magnesium hydroxides, silicic acids including highly-dispersed silicic acids from pyrolysis processes, carbon black including blacks produced industrially, graphite, metal powders such as aluminum, copper, iron, silver or steel, PVC powder or hollow beads;

fibers in particular glass fibers, carbon fibers, metal fibers, ceramic fibers or plastic fibers such as polyamide [nylon] fibers or polyethylene fibers;

pigments, for example, titanium dioxide or iron oxides;

rheology modifiers such as in particular thickeners, for example, layered silicates, such as bentonite, derivatives of castor oil, hydrogenated castor oil, polyamides, polyurethanes, urea compounds, pyrogenic silicic acids, cellulose ethers and hydrophobically modified polyoxy ethylenes;

desiccants such as in particular molecular sieves, calcium oxide, highly reactive isocyanates such as p-tosyl isocyanates, orthoformic acid esters, alkoxy silanes such as tetraethoxy silane, organoalkoxy silanes such as vinyl trimethoxy silane and organoalkoxy silanes having a functional group in a position to the silane group;

adhesive promoters, for example, organoalkoxy silanes such as aminosilanes, mercaptosilanes, epoxy silanes, vinyl silanes, (meth)acryl silanes, isocyanatosilanes, carbamatosilanes, alkyl silanes, S-(alkylcarbonyl)mercaptosilanes and aldiminosilanes as well as oligomeric forms of these silanes in particular 3-glycidoxy propyltrimethoxysilane, 3-aminopropyl trimethoxy silane, N-(2-amino ethyl)-3-aminopropyl trimethoxy silane, N-(2-amino ethyl)-N'-[3-(trimethoxysilyl)propyl]ethylene diamine, 3-mercaptopropyltrimethoxy silane, 3-isocyanatopropyltrimethoxy silane, 3-ureidopropyltrimethoxy silane, 3-chloropropyltrimethoxy silane, vinyl trimethoxy silane or the corresponding organosilanes with ethoxy groups instead of methoxy groups;

stabilizers against oxidation, heat, light and UV radiation;

flame retardant substances such as those listed below as possible components of an epoxy resin composition Z2;

surface-active substances such as, for example, wetting agents, flow control agents, deaerating agents or foam suppressants and biocides such as, for example, algicides, fungicides or substances that inhibit the growth of fungus.

The composition Z1 containing isocyanate groups preferably contains additional additive and auxiliary substances in particular fillers, pigments and stabilizers.

The composition Z1 containing isocyanate groups preferably contains only a small amount of catalyst, in particular a metal-based catalyst content of less than 0.02% by weight metal. This composition is in particular essentially free of catalysts to increase the curing speed, in particular organometal compounds such as dimethyl tin dilaurate and similar organo tin compounds.

The composition Z1 containing isocyanate groups preferably has only a low solvent content, especially preferably less than 10% by weight, in particular less than 5% by weight of solvent. The composition Z1 containing isocyanate groups is most especially preferably essentially free of solvents.

The composition Z1 containing isocyanate groups is advantageously present in the form of a two-component composition.

The term "two-component" is understood to denote a curable compound in which the ingredients of the curable compound are present in two separate components, each of which is stored in a separate container. The two components are not mixed together until shortly before or during the application of the curable compound, whereupon the compound that has been mixed will cur, optionally under the influence of moisture.

A two-component composition Z1 consists of a first component containing isocyanate groups and having at least one polyisocyanate, optionally in the form of an adduct AD2 and a second component which is free of isocyanate groups and contains at least one curing agent compound HV, optionally in the form of an amine of formula (I) or an adduct AD1. Other components of the composition Z1, for example, catalysts or the above mentioned additive and auxiliary substances may be present as part of the first or second component. It is advantageous to be sure that such additional components do not severe impair the stability of the respective component in storage. This means that these components and/or ingredients must not trigger the reactions that result in curing to any significant extent during storage. In particular this means that substances which are used as part of the first component containing isocyanate groups should not contain any water at all or at most only traces of water. It may be advisable to chemically of physically dry certain ingredients before mixing them into the composition.

The two components are prepared separately from one another and in the absence of moisture at least for the first component containing the isocyanate groups. The two components are stable in storage separately from one another until they are used, i.e., each of them may be stored in a suitable package or arrangement such as drum, a bag, a bucket, a cartridge or a vial for several months or up to a year or even more without any change in their respective properties which would be relevant for their use.

To use a two-component composition Z1, the two components are mixed together. In doing so, the mixing ratio between the two components is selected so that the groups that are reactive with isocyanate groups are present in a suitable ratio to the isocyanate groups. The ratio of the number of groups of the second component that are reactive with isocyanate groups to the number of isocyanate groups of the first component is suitably in the range of 0.5 to 1.1, in particular 0.6 to 1.0. The mixing ratio between the first and second components is usually in the range of 1:10 to 10:1 parts by weight.

The two components are mixed together by a suitable method which may be either a continuous process or a batch process. If the mixing is performed before application, it is important to be sure that not too much time elapses between mixing the components and their application because this can lead to problems such as a delayed or incomplete buildup of adhesion with the substrate. The mixing may be performed at room temperature which is typically in the range from approximately −20° C. to 50° C. preferably at approximately −10° C. to 30° C. However, the components may also be heated prior to mixing, for example, heated to a temperature in the range of 30° C. to 80° C., so that in particular the viscosity of the components is reduced. This is advantageous in particular in the case of application by a spray method.

The curing of the composition Z1 begins with the mixing of the two components in that primary and secondary amino groups, hydroxyl groups and mercapto groups present in the composition begin to react with the isocyanate groups that are present. Excess isocyanate groups will react with moisture.

Thus the present invention also describes a fully cured composition, which is obtained by reacting at least one polyisocyanate with at least one curing agent compound HV of a composition Z1 containing isocyanate groups such as those described above.

The compositions Z1 in the form of the variants that have already been described have various advantageous and surprising properties.

If the composition Z1 is in such a form that it contains at least one amine of formula (I) in addition to at least one polyisocyanate P, then it will have a slight amine odor, will have a comparatively low viscosity and will have a high rate of curing with a comparatively long processing time for secondary aliphatic amines. In the case of aliphatic polyisocyanates P, their processing time will be long enough so that the components can be mixed in batches and applied at leisure. Therefore the composition can be used without expensive application equipment that is difficult to operate and in particular need not be applied by a spray method, which is advantageous for toxicological reasons. In the case of aromatic polyisocyanates P the processing time is of course shorter but is still long enough in application in a spray method to ensure good flow of the composition applied and good wetting of the substrate to which the composition is applied. In the case of amines of formula (I b) containing ester groups, compositions Z1 containing aromatic polyisocyanates P and having a comparatively long processing time are also accessible. Therefore, when using such curing agents, it is not necessary to use isocyanates such as 2,4'-MDI and MDI isomer mixtures enriched with the 2,'4-isomer and having a reduced reactivity, thus permitting substantial cost savings. Furthermore, the components of such compositions Z1, which are based on aromatic polyisocyanates, may also be mixed in batches.

The curing of such a composition proceeds very rapidly so that post-processing is possible after only a short period of time. Post-processing in the case of a coating, for example, may consist of inspection or grinding or applying another layer, or in the case of adhesive bonding, it may consist of applying a load to the adhesive bond in the form of its own weight, so that fastening devices, for example, can be removed and the adhesively bonded parts can be moved, or in the case of a cast composition, this may consist of a molding, so that the mold is free for further use. This composition also cures fully even in the presence of high atmospheric humidity without any foaming. In the case of a flat surface application, high-quality films with a high hardness and elasticity and good adhesion to various substrates are obtained, forming coatings having in particular an excellent resistance to abrasion, moisture and chemicals such as organic or inorganic acids, bases or solvents. In the case of aliphatic polyisocyanates P, the fully cured films also have excellent light stability without any tendency to yellowing.

In the case of the composition Z1, it may also contain, in addition to at least one polyisocyanate P, at least one adduct AD1 with a polyisocyanate and then the composition will fundamentally have a reduced sensitivity to unwanted influences during curing and will cure even faster while the processing time remains approximately the same because some of the polyisocyanates will have already been reacted with an amine of formula (I) and thus the number of reactions required for curing the composition will have been reduced. Another advantage is that the amounts of the two components of the composition by weight or by volume can be adjusted more easily to a desired mixing ratio between the first and second components. For machining application in particular, it is often necessary to maintain a predetermined mixing ratio through the application equipment, which is difficult under some circumstances according to the state of the art in particular when the composition is supposed to be free of solvent.

In the case of a composition Z1, such that it contains at least one polyisocyanate in the form of an adduct AD2 in addition to at least one curing agent compound HV—i.e., this adduct is an amine of formula (I) in a completely converted form as part of the first component containing the isocyanate groups—this will yield similar advantages with regard to the sensitivity during curing, the curing rate and the adjustment of the missing ratio as described above. Based on their excellent diluent and elastifying properties, adducts AD2 which are derived from amines of formula (I b) are especially advantageous.

The compositions Z1 are suitable for a number of applications, in particular as casting components, sealants, adhesives, coatings, linings, paints, lacquers, seals, primers, foundations and foams for construction and industrial application. They are suitable in particular for applications, which have a low solvent content or should even be solvent-free as well as for applications in which a coating is to be applied by a machine in particular by a spray method.

In addition, the advantageous properties of the compositions Z1 described here make is possible for the cured compositions to have a high urea group content. Such compositions Z1 are also known as polyurea compositions in the state of the art. They cure even at low temperatures and in the presence of a high atmospheric humidity mostly without problems and have a high hardness and excellent stability in the cured form. They are therefore especially suitable for applications which make especially high demands with regard to strength and stability, e.g., as floor coverings and as coatings for floors of interior rooms such as offices, industrial buildings, gymnasiums or refrigeration rooms, or in the exterior area for balconies, terraces, parking lots, bridges or roofs and as protective coatings for concrete, cement, metals or plastics for example, for surface sealing of loading surfaces, tanks, silos, shafts, pipelines or tubing lines, where these coatings protect the respective substrates in particular from corrosion, abrasion, moisture and/or chemicals and as surface sealing for such coatings. If the compositions Z1 contain mostly or exclusively polyisocyanates P with aliphatic isocyanate groups, then the fully cured compositions have an excellent light stability, so that they hardly yellow at all even with prolonged light exposure. Such compositions Z1 are especially suitable for surface sealing, top coats or the surface layer of paints, coatings.

The composition Z1 described here is applied to at least one substrate S, the following materials being particularly suitable as substrate S:

glass, glass ceramics, concrete, mortar, baked brick, tile, plaster and natural stone such as granite or marble;

metals and metal alloys such as aluminum, iron, steel and nonferrous metals as well as surface-finished metals and alloys such as galvanized or chrome-plated metals;

leathers, textiles, paper, wood, wood-based materials bound with resins, for example, phenolic resins, melamine or epoxy resins, resin-textile composite materials and other so-called polymer composites;

plastics such as polyvinyl chloride (hard and soft PVC), acrylonitrile-butadiene styrene copolymers (ABS), polycarbonate (PC), polyimide (PA), polyester, poly(methylmethacrylate) (PMMA), polyesters, epoxy resins, polyurethanes (PUR), polyoxymethylene (POM), polyolefins (PO), polyethylene (PE) or polypropylene (PP), ethylene-propylene copolymers (EPM) and ethylene-propylene diene terpolymers (EPDM) where the plastics may preferably be surface treated by means of plasma, corona or flames;

fiber-reinforced plastics such as carbon fiber reinforced plastics (CFP), glass fiber reinforced plastics (GFP) and sheet molding compounds (SMC);

coated substrates such as powder-coated metals or alloys;

paints and varnishes, in particular automotive top coat enamels.

The substrates may be pretreated, if necessary, before applying the composition Z1. Such pretreatments include in particular physical and/or chemical cleaning methods, for example, grinding, sandblasting, blasting with beads, brushes or the like such that the resulting dust is advantageously removed by suction, as well as, additionally, treating with cleaning agents or solvents or applying an adhesion promoter, an adhesion promoter solution or a primer.

A composition Z1 containing isocyanate groups may be used in a method for coating surfaces. The components of the composition Z1 are therefore mixed with one another using a suitable method and the mixed composition is applied to a substrate in a layer thickness of a few micrometers up to approximately 5 mm. Depending on the reactivity of the composition Z1, various methods for coating are suitable. Compositions Z1 with a relatively long processing time may be mixed in batches and the mixed composition may then be applied immediately by roller or by doctor blade or squeegee to a substrate in the desired layer thickness. However, they may also be applied by a spray method. Compositions Z1 with a shorter processing time are suitably applied in a spray method in which both a conventional spray method and an airless spray method are possible. Multicomponent spray systems, by means of which the components of the composition Z1 are mixed together immediately before being sprayed are especially suitable. To reduce the viscosity of the composition Z1 it may be advantageous to heat the components before mixing them to a temperature in the range of 40° C. to 80° C., for example, and/or to dilute them with a suitable solvent. The composition Z1 may be applied a as a coating in one layer, but it may also be applied in several layers in multiple operations. It may also be advantageous to apply a structure of several layers each having a different composition of the coating such that the composition may be applied either as the bottom layer, as an intermediate layer or as the top layer. A composition Z1 may be used in particular as a protective coating for concrete, in particular on bridges in which case the composition is typically sprayed on.

Another subject matter of the invention is a curable compound in the form of an epoxy resin composition Z2 containing a) at least one epoxy resin and
b) at least amine of formula (I).

An epoxy resin composition Z2 is especially suitable as a coating.

An "epoxy group" is understood to refer to the structural element

A "glycidyl ether" is understood to refer to an ether of 2,3-epoxy-1-propanol (glycidol).

The abbreviation "EEW" stands for "epoxy equivalent weight."

Amines of formula (I a), amines of formula (I c) and amines of formula (I d) are preferably part of an epoxy resin composition Z2.

Suitable epoxy resins include the epoxy resins that are typically used in epoxy chemistry. These are obtained by known methods, for example, by oxidation of the corresponding olefins or by reaction of epichlorohydrin with the corresponding polyols, polyphenols or amines.

Especially suitable as the epoxy resin are the so-called polyepoxy liquid resins, hereinafter referred to as "liquid resin." These have a glass transition temperature which is usually below 25° C. in contrast with so-called solid resins which have a glass transition temperature above 25° C. and can be pulverized to free-flowing bulk powders at 25° C.

In one embodiment the liquid resin is an aromatic polyepoxy. For example, liquid resins of formula (XIII) are suitable for this:

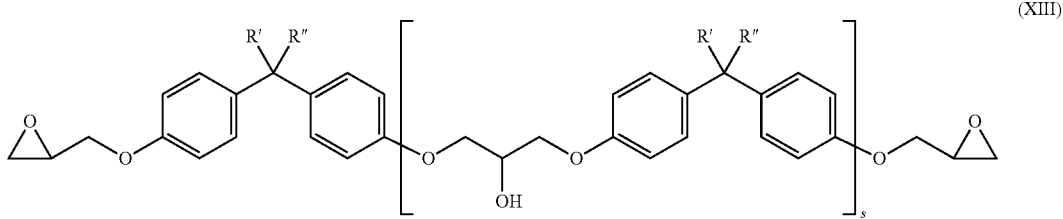

wherein R' and R" independently of one another each stand for a hydrogen atom or a method group and x stands for a value of 0 to 1 on the average. Liquid resins of formula (XIII) in which the index s stands for a value of less than 0.2 on the average are preferred.

The liquid resins of formula (XIII) are diglycidyl ethers of bisphenol A, bisphenol F and bisphenol A/F, where A stands for acetone and F stands for formaldehyde which serve as reagent for the synthesis of these bisphenols. Accordingly a bisphenol A liquid resin contains methyl groups, a bisphenol F liquid resin contains hydrogen atoms and a bisphenol A/F liquid resin contains both methyl groups and hydrogen atoms as R' and R" in formula (XIII). In the case of bisphenol F there may also be positional isomers, in particular those derived from 2,4'- and 2,2'-hydroxyphenyl methane.

Other suitable aromatic liquid resins include the glycidylation products of dihydroxybenzene derivatives such as resorcinol, hydroquinone and pyrocatechol;

additional bisphenols or polyphenols such as bis-(4-hydroxy-3-methylphenyl)methane, 2,2-bis-(4-hydroxy-3-methyl phenyl) propane (bisphenol bis-(3,5-dimethyl-4-hydroxyphenyl) methane, 2,2-bis-(3,5-dimethyl-4-hydroxyphenyl) propane, 2,2-bis-(3,5-dibromo-4-hydroxyphenyl) propane, 2,2-bis-(4-hydroxy-3-tert-butylphenyl) propane, 2,2-bis-(4-hydroxyphenyl) butane (bisphenol B), 3,3-bis-(4-hydroxyphenyl)pentane, 3,4-bis-(4-hydroxyphenyl) hexane, 4,4-bis-(4-hydroxyphenyl) heptane, 2,4-bis-(4-hydroxyphenyl)-2-methyl butane, 2,4-bis-(3,5-dimethyl-4-hydroxyphenyl)-2-methyl butane, 1,1-bis-(4-hydroxyphenyl)cyclohexane (bisphenol Z), 1,1-bis-(4-hydroxyphenyl)-3,3,5-trimethyl cyclo hexane (bisphenol TMC), 1,1-bis-(4-hydroxyphenyl) 1-phenylethane, 1,4-bis[2-(4-hydroxyphenyl)-2-propyl]benzene) (bisphenol P), 1,3-bis-[2-(4-hydroxyphenyl)-2-propyl]benzene) (bisphenol M), 4,4'-dihydroxydiphenyl (DOD), 4,4'-dihydroxy benzophenone, bis-(2-hydroxynaphth-1-yl) methane, bis-(4-hydroxynaphth-1-yl) methane 1,5-dihydroxynaphthalene, tris-(4-hydroxyphenyl) methane, 1,1,2,2-tetrakis=(4-hydroxyphenyl)ethane, bis-(4-hydroxyphenyl)ether, bis-(4-hydroxyphenyl)sulfone;

condensation products of phenols with formaldehyde which are obtained under acidic conditions such as phenol novolacs or cresol novolacs, often known as bisphenol F novolacs;

aromatic amines such as aniline, toluidine, 4-aminophenol, 4,4'-methylene diphenyl diamine (MDA), 4,4'-methylene diphenyl di-(N-methyl)amine, 4,4'-[1,4-phenylene bis-(1-methyl ethylidene)]bis-aniline (bis-aniline P), 4,4'-[1,3-phenylene bis-(1-methyl ethylidene)]bis-aniline (bis-aniline M).

Also suitable as the epoxy resin is an aliphatic or cycloaliphatic polyepoxy such as

- a glycidyl ether of a saturated or unsaturated, branched or unbranched, cyclic or open chain $C_2$ to $C_{30}$ diol such as, for example, ethylene glycol, propylene glycol, butylene glycol, hexane diol, octane diol, polypropylene glycol, dimethylol cyclo hexane, neopentyl glycol or dibromo neopentyl glycol;
- a glycidyl of a tri- or tetrafunctional saturated or unsaturated branched or unbranched cyclic or open chain polyol such as castor oil, trimethylolpropane, trimethylolethane, pentaerythritol, sorbitol or glycerol as well as alkoxylated glycerol or alkoxylated trimethylolpropane;
- a hydrogenated bisphenol A, F or A/F liquid resin, for example, the glycidylization products of hydrogenated bisphenol A, F or A/F;
- an N-glycidyl derivative of amides or heterocyclic nitrogen bases such as triglycidyl cyanurate and triglycidyl isocyanurate as well as the reaction product of epichlorohydrin and hydantoin.

Also suitable for use as the epoxy resin are a bisphenol A, F or A/F solid resin having a structure similar to that of the liquid resins of formula (XIII) defined above but having a value of 2 to 12 instead of the index s and having a glass transition temperature above 25° C.

Finally epoxy resins obtained by oxidation of olefins, for example, the oxidation of vinyl cyclo hexene, dicyclo pentadiene, cyclo hexadiene, cyclo dodecadiene, cyclo dodecatriene, isoprene, 1,5-hexadiene, butadiene, polybutadiene or divinyl benzene are also suitable as the epoxy resin.

The preferred epoxy resins are liquid resins based on a bisphenol, in particular based on bisphenol A, bisphenol F or bisphenol A/F such as those which are commercially available from Dow, Huntsman and Hexion, for example, such that the latter are actually present in combination with bisphenol A solid resin or bisphenol F novolac epoxy resin.

The epoxy resin may contain a reactive diluent, in particular an epoxy reactive diluent. Suitable examples of epoxy reactive diluents include low viscosity mono- and polyepoxies such as the polyglycidyl ether of monovalent or polyvalent phenols and aliphatic or cycloaliphatic alcohols such as in particular to the polyglycidyl ethers of diols or polyols mentioned above and also in particular phenyl glycidyl ether, cresyl glycidyl ether, p-n-butylphenyl glycidyl ether, p-tert-butyl-phenyl glycidyl ether, nonyl phenyl glycidyl ether, allyl glycidyl ether, butyl glycidyl ether, hexyl glycidyl ether, 2-ethylhexylglycidyl ether as well as glycidyl ethers of natural alcohols such as, for example, $C_8$ to $C_{10}$ alkyl glycidyl ethers or $C_{12}$ to $C_{14}$ alkyl glycidyl ethers. Adding a reactive diluent to the epoxy resin causes a reduction in viscosity and—in the fully cured state of the epoxy resin composition a reduction in the glass transition temperature and in the mechanical values.

The epoxy resin composition Z2 may also contain additional compounds that are reactive with epoxy groups in particular additional amines and especially compounds having mercapto groups in addition to at least one epoxy resin and at least one amine of formula (I).

In particular the following are suitable as the additional compounds that are reactive with epoxy groups—in addition to the amines of formula (I) as described above:

- primary aliphatic polyamines, amino alcohols and amino thiols such as in particular the amines PA of formula (II) already described above, as long as they have at least two groups that are reactive with isocyanate groups;
- secondary aliphatic polyamines such as those already mentioned above as the possible curing agent compound HV of a composition Z1 containing isocyanate groups;
- primary and/or secondary aromatic amines such as those already mentioned above as the possible curing agent compound HV of a composition Z1 containing isocyanate groups;
- amine/epoxy adducts, in particular the adducts of the polyamines mentioned above with diepoxy in a molar ratio of at least 2:1, in particular in a molar ratio of 2:1 to 6:1, as well as the reaction products of amines and epichlorohydrin, in particular those of 1,3-xylylene diamine, available commercially as Gaskamine® 328 (from Mitsubishi);
- polyamidoamines, which are the reaction products of a monovalent or polyvalent carboxylic acid and/or the esters or anhydrides thereof, in particular a dimer fatty acid and an aliphatic, cycloaliphatic or aromatic polyamine used in a stoichiometric excess, in particular a polyalkylene amine such as, for example, DETA or TETA, in particular the commercially available polyamidoamine Versamid® 100, 125, 140 and 150 (from Cognis), Aradur® 223, 250 and 848 (from Huntsman), Euretek® 3607, Euretek® 530 (from Huntsman), Beckopox® EH 651, EH 654, EH 655, EH 661 and EH 663 (from Cytec);
- liquid mercaptan-terminated polysulfide polymers, which are known by the brand names Thiokol® (from Morton Thiokol, available from SPI Supplies or from Toray Fine Chemicals, for example), in particular the grades LP-3, LP-33, LP-980, LP-23, LP-55, LP-56, LP-12, LP-31, LP-32 and LP-2 as well as those also known by the brand names Thioplast® (from Akzo Nobel), in particular the grades G 10, G 112, G 131, G 1, G 12, G 21, G 22, G 44 and G 4;
- mercaptan-terminated polyoxy alkylene ethers, obtained, for example, by reaction of polyoxy alkylene diols and triols either with epichlorohydrin or with an alkylene oxide, followed by sodium hydrogen sulfide;
- mercaptan-terminated epoxy curing agents in the form of polyoxy alkylene derivatives known by the brand names Capcure® (from Cognis), in particular the grades WR-8, LOF and 3-800;
- polyesters of thiocarboxylic acids, for example, the pentaerythritol tetramercapto acetate, trimethylol propane trimercapto acetate, glycol dimercaptoacetate, pentaerythritol tetra-(3-mercaptopropionate), trimethylol propane tri-(3-mercaptopropionate) and glycol di-(3-mercapto propionate) as well as the esterification products of polyoxy alkylene diols and triols, ethoxylated trimethylolpropane and polyester diols with thio carboxylic acids such as thio glycolic acid and 2- or 3-mercapto propionic acid;
- additional compounds having mercapto groups, such as in particular 2,4,6-trimercapto-1,3,5-triazine, 2,2'-(ethylene dioxy)diethanethiol (triethylene glycol dimercaptan) and ethane dithiol.

Additional compounds that are reacted with epoxy groups preferably include DAMP, MPMD, C11-neodiamine, 1,6-hexane diamine, TMD, 1,12-dodecane diamine, 1,3-diamino cyclo hexane, $H_{12}$-MDA, bis-(4-amino-3-methyl cyclo hexyl) methane, IPDA, 1,3-xylylene diamine, N,N'-bis(phenylethyl)-1,3-xylylene diamine (Gaskamine® 240), polyoxy alkylene diamine and triamine in particular the grades Jeffamine® D-230, Jeffamine® D-400 and Jeffamine® T-403 as well as amine-epoxy adducts, in particular Gaskamine® 328.

The epoxy composition Z2 optionally contains additional ingredients in particular the additives and auxiliary substances typically used in epoxy resin compositions, for example, the following:

- solvents, film-forming aids or extenders such as toluene, xylene, methyl ethyl ketone, 2-ethoxyethanol, 2-ethoxyethylacetate, benzyl alcohol, ethylene glycol, diethylene glycol butyl ether, dipropylene glycol butyl ether, ethylene glycol butyl ether, ethylene glycol phenyl ether, N-methylpyrrolidone, propylene glycol butyl ether, propylene glycol phenyl ether, diphenyl methane, diisopropyl naphthalene, petroleum fractions such as, for example, Solvesso® grades (from Exxon), aromatic hydrocarbon resins in particular the grades containing phenol groups, sebacates, phthalates, organic phosphoric and sulfonic acid esters and sulfonamides;
- reactive diluents, for example, epoxy reactive diluents such as those already mentioned above, epoxidized soybean oil or linseed oil, compounds containing acetoacetate groups, in particular acetoacetylated polyols, butyrolactone and also silicones containing isocyanates and reactive groups;
- polymers such as, for example, polyamides, polysulfides, polyvinyl formal (PVF), polyvinylbutyral (PVB), polyurethanes (PUR), polymers with carboxyl groups, polyamides, butadiene acrylonitrile copolymers, styrene acrylonitrile copolymers, butadiene styrene copolymers, homo- or copolymers of unsaturated monomers in particular from the group comprising ethylene, propylene, butylene, isobutylene, isoprene, vinyl acetate and alkyl(meth)acrylates, in particular chlorosulfonated polyethylenes and polymers containing fluorine, sulfonamide-modified melamines and purified montan waxes;
- organic and inorganic fillers, for example, ground or precipitated calcium carbonates which are optionally coated with fatty acids in particular stearates, barite (heavy spar), talc, quartz powders, quartz sand, dolomites, wollastonites, kaolins, mica (potassium-aluminum-silicate), molecular sieves, aluminum oxides, aluminum hydroxides, magnesium hydroxide, silicic acids, cements, gypsums, fly ashes, carbon black, graphite, metal powders such as aluminum, copper, iron, silver or steel, PVC powder or hollow beads;
- fibers, in particular glass fibers, carbon fibers, metal fibers, ceramic fibers or plastic fibers such as polyamide fibers or polyethylene fibers;
- pigments, for example, titanium dioxide and iron oxides;
- accelerators which accelerate the reaction between amino groups and epoxy groups, for example, acids or compounds that can be hydrolyzed to yield acids, for example, organic carboxylic acids such as acetic acid, benzoic acid, salicylic acid, 2-nitro benzoic acid, lactic acid, organic sulfonic acids such as methane sulfonic acid, p-toluene sulfonic acid or 4-dodecyl benzene sulfonic acid, sulfonic acid esters, other organic or inorganic acids such as, for example, phosphoric acid or mixtures of the acids and acid esters mentioned above; also tertiary amines such as 1,4-diazabicyclo[2.2.2]octane, benzyl dimethyl amine, α-methylbenzyl dimethyl amine, triethanol amine, dimethyl aminopropyl amine, imidazoles such as in particular N-methyl imidazole, N-vinyl imidazole or 1,2-dimethyl imidazole, the salts of such tertiary amines, quaternary ammonium salts such as, for example benzyl trimethyl ammonium chloride, phenols in particular bisphenols, phenolic resins and Mannich bases such as, for example 2-(dimethyl amino methyl) phenol and 2,4,6-tris-(dimethyl amino methyl) phenol, phosphites such as, for example, di- and triphenyl phosphites as well as compounds containing mercapto groups such as those already mentioned above;
- rheology modifiers such as in particular thickeners, for example, layered silicates such as bentonites, derivatives of castor oil, hydrogenated castor oil, polyamides, polyurethanes, urea compounds, pyrogenic silicic acids, cellulose ether and hydrophobically modified polyoxyethylenes;
- adhesion promoters, for example, organoalkoxy silanes such as aminosilanes, mercaptosilanes, epoxy silanes, vinyl silanes, (meth)acryl silanes, isocyanate silanes, carbamato silanes, alkyl silanes, S-(alkylcarbonyl) mercaptosilanes and aldiminosilanes as well as oligomeric forms of these silanes in particular 3-glycidoxy propyl trimethoxy silane, 3-aminopropyl trimethoxy silane, N-(2-amino ethyl)-3-aminopropyl trimethoxy silane, N-(2-amino ethyl)-N'-[3-(trimethoxysilyl) propyl]ethylene diamine, 3-mercaptopropyl trimethoxy silane, 3-isocyanatopropyl trimethoxy silane, 3-ureidopropyltrimethoxy silane, 3-chloropropyl trimethoxy silane, vinyl trimethoxy silane or the corresponding organosilanes with ethoxy groups instead of methoxy groups;
- stabilizers against oxidation, heat, light and UV radiation;
- flame retardant substances in particular compounds such as aluminum hydroxide ($Al(OH)_3$ also known as ATH for aluminum trihydrate), magnesium hydroxide ($Mg(OH)_2$ also known as MDH for magnesium dihydrate), ammonium sulfate (($NH_4)_2SO_4$), boric acid ($B(OH)_3$), zinc borate, melamine borate and melamine cyanurate; compounds containing phosphorus such as ammonium phosphate (($NH_4)_3PO_4$), ammonium polyphosphate, melamine phosphate, melamine pyro phosphate, triphenyl phosphate, diphenyl cresyl phosphate, tricresyl phosphate, trimethyl phosphate, tris-(2-ethylhexyl) phosphate, trioctyl phosphate, mono-, bis- and tris-(isopropyl phenyl)phosphate, resorcinol-bis(diphenyl phosphate), resorcinol diphosphate oligomer, tetraphenyl resorcinol diphosphite, ethylene diamine diphosphate and bisphenol A-bis(diphenyl phosphate); compounds that contain halogen such as chloro alkyl phosphates in particular, for example, tris-(chloroethyl)phosphate, tris-(chloropropyl)phosphate and tris-(dichloro isopropyl)phosphate, polybrominated diphenyl ether in particular decabromo diphenyl ether, polybrominated diphenyl oxide, tris-[3-bromo-2,2-bis(bromomethyl) propyl] phosphate, tetrabromo bisphenol A, bis-(2,3-dibromopropyl ether) of bisphenol A, brominated epoxy resins, ethylene-bis-(tetrabromo phtalimide), ethylene-bis-(dibromo norbornene dicarboximide), 1,2-bis-(tribromo phenoxy)ethane, tris-(2,3-dibromopropyl) isocyanurate, tribromophenol, hexabromo cyclododecane, bis-(hexachlorocyclopentadieno)cyclooctane and chloroparaffins as well as combinations of a halogen compound and antimony trioxide ($Sb_2O_3$) or antimony pentoxide ($Sb_2O_5$);
- surface-active substances such as, for example, wetting agents, flow control agents, aeration agents or foam suppressants;
- biocides such as, for example, algicides, fungicides or substances that inhibit the growth of fungus.

The epoxy resin composition Z2 preferably contains additional additives and auxiliary substances, in particular wetting agents, flow control agents, foam suppressants, stabilizers, pigments and accelerators in particular salicylic acid or 2,4,6-tris-(dimethylamino methyl)phenol.

The epoxy resin composition Z2 preferably contains only a small amount of solvents especially preferably less than 10% by weight, in particular less than 5% by weight solvents. The composition is most preferably essentially free of solvents, where the term "solvent" in the present document also includes substances such as benzyl alcohol and alkyl phenols.

The epoxy resin composition Z2 is advantageously in the form of two-component composition.

A two component epoxy resin composition Z2 consists of a so-called resin component containing at least one epoxy resin and a so-called curing agent component, which contains at least one amine of formula (I) and optionally other compounds that are reactive with epoxy groups.

Other ingredients of a two-component epoxy resin composition Z2 may be present as a part of the resin or curing agent component.

The resin component and the curing agent component of a two-component epoxy resin composition Z2 may each be stored in a suitable package or configuration such as, for example, a drum, a task, a bag, a bucket, a basket, a cartridge or a tube for several months up to a year or even longer prior to their application without undergoing any changes in their respective properties of an extent that would be relevant for their use.

For use of a two-component epoxy resin composition Z2, the resin component and the curing agent component are mixed together shortly before or during application. The mixing ratio between the two components is preferably selected so that the groups of the curing agent component that are reactive with epoxy groups are in a suitable ratio to the epoxy groups of the resin component.

The ratio of the number of groups of the curing agent components that are reactive to epoxy groups in relation to the number of epoxy groups of the resin component is suitably in the range of 0.5 to 1.5, in particular 0.8 to 1.2.

Those skilled in the art are aware that primary amine groups are difunctional with respect to epoxy groups and that a primary amino group thus counts as two reactive groups with respect to epoxy groups.

In parts by weight, the mixing ratio between the resin component and the curing agent component is usually in the range of 1:10 to 10:1.

The two components are mixed by a suitable method which may be either continuous or batch process. If the mixing is performed before application it is important to be sure that not too much time elapses between the mixing of the components and their application because this can lead to problems, for example, a delay or incomplete buildup of adhesion to the substrate. The mixing is preferably performed at room temperature which is typically in the range from approximately 0 to 50° C., preferably approximately 10 to 30° C. for application of an epoxy resin composition.

Curing of the epoxy resin composition Z2 described here begins when the two components are mixed by chemical reaction. Then the NH hydrogen atoms of the amines of formula (I) that are present in the mixed composition and optionally any other groups that are reactive with epoxy groups are reacted with the epoxy groups, causing ring opening of same (addition reaction). As a result of these reactions, the composition polymerizes and ultimately cures.

Curing takes place in particular at room temperature, which is typically in the range of approximately 0 to 50° C., preferably at approximately 10° C. to 30° C.

The curing typically extends over a period of a few days to weeks until it is largely concluded under the given conditions. The duration depends on, among other things, the temperature, the reactivity of the ingredients and their stoichiometric ratio as well as the presence of accelerators.

Thus the present invention also describes a fully cured composition, which is obtained by reaction of at least one epoxy resin with at least one amine of formula (I) of an epoxy resin composition Z2 such as that described above.

The epoxy resin composition Z2 described here is applied to at least one substrate, the substrate S already mentioned above being suitable. The substrates S may be pretreated as needed before application of the epoxy resin composition, as already described above.

The amities of formula (I) contained in the epoxy resin compositions Z2 are typically low viscosity substances with a low volatility and low odor, as mentioned above and have a surprisingly good compatibility with the usual commercial epoxy resins. Without restricting the present invention in any way it is assumed that the good compatibility can be attributed at least in part to the influence of the groups on the ends of the molecules introduced with the aldehydes ALD of formula (III) that are used in the reductive alkylation.

An epoxy resin composition Z2 may be used in a method for coating. The epoxy resin composition Z2 therefore advantageously has a liquid consistency with good flow properties. It may therefore be applied to predominantly flat surfaces in particular as a self-leveling coating, for example, as a floor covering. As a result, the composition has a low viscosity at the time of application. The viscosity of the epoxy resin composition Z2 at the time of application—i.e., immediately after mixing the resin component with the curing agent component—is preferably in a range of 100 to 3000 mPa·s, in particular in the range of 100 to 2000 mPa·s, most preferably in the range of 100 to 1500 mPa·s, measured with a cone-plate viscometer at 20° C. Such a viscosity is comparatively low for an epoxy resin composition and can usually be achieved only by using low viscosity curing agents if the use of solvents and diluents is to be omitted entirely. Therefore it is an essential aspect of the present invention that the amities of formula (I) are typically liquid and low-viscosity compounds.

Before application the resin component and the curing agent component are mixed together by a suitable method and the mixed composition is applied to a substrate as a thin flat film with a layer thickness of typically approximately 50 μm to approximately 5 mm, typically at room temperature, and doing so within the processing time. The application takes place, for example, by pouring the mixture onto the substrate that is to be coated. The mixed composition in the liquid state is distributed uniformly with the help of a squeegee or a trowel. In addition, the mixed distributed composition may be leveled with a roller and aerated. However, application by machine, for example, by spray application is also possible.

Application of a mixed two-component epoxy resin composition Z2 by brush, cloth, sponge or spray gun to a substrate is likewise possible especially if the composition is to be applied in a thin layer of less than 1 mm, for example, as a primer coat or as a surface seal. For such an application, the composition Z2 will usually contain a solvent.

Typically the films formed after curing are largely clear, glossy, non-tacky films having excellent mechanical properties such as a high hardness, good scratch resistance and toughness as well as good adhesion to various substrates. In contrast with that, epoxy resin compositions according to the state of the art which contain curing agents with mainly primary amino groups instead of the amine of formula (I)

often cure to form films with blushing-related surface defects such as roughness, spottiness, cloudiness and tackiness.

Due to the use of the amines of formula (I) as curing agent, self-flow epoxy resin coatings which need only relatively small amounts of diluting additives such as solvents or none at all are thus accessible. In addition, the primary amino group content in the coatings can be kept so low that there are hardly any reactions at all with atmospheric $CO_2$. Therefore blushing effects are largely suppressed in large area application even under unfavorable conditions, i.e., reaction conditions that promote blushing namely at a low curing temperature, for example, in the range of 0 to 10° C. and at high atmospheric humidity. It is therefore possible to largely or completely omit the addition of additives according to the state of the art which reduce blushing and are not covalently bound in the composition in curing and can outgas as VOC, such as in particular benzyl alcohol. The epoxy resin compositions Z2 described here can thus also be used to advantage even in interior rooms.

The epoxy resin composition Z2 described here may be used as casting compound, sealants, adhesives, primers or foams as well as in particular for large area application in particular as floor coverings, coating, paints, enamels, seals and primers for building and industrial applications, for example, as floor coverings and floor coatings for interior rooms such as offices, industrial buildings, gymnasiums or refrigeration rooms or in the exterior area for balconies, terraces, parking lots, bridges or roofs as well as being used as protective coatings for concrete or metals in particular as a protective paint against corrosion as well as for surface seals for such coatings.

In these applications their excellent properties are manifested, such as water fastness, corrosion resistance, adhesion, chemical stability and/or hardness and toughness as well as in particular their excellent properties with respect to large area curing to form largely clearly glossy and non-tacky films without blushing-related surface defects.

EXAMPLES

1. Description of the Measurement Methods

The amine content, i.e., the total free amino group and blocked amino group (imino group) content in the compound produced was determined by titration (using 0.1N $HClO_4$ in glacial acetic acid against crystal violet) and is always reported in mmol N/g.

Infrared spectra were recorded as undiluted films (the substance was dissolved in $CH_2Cl_2$, if necessary, and then the solvents were evaporated and the remaining substances were applied to an FT-IR 1600 apparatus from Perkin Elmer equipped with a horizontal ATR measuring unit with a ZnSe crystal; the absorption bands are given in wavenumbers ($cm^{-1}$) (measurement window 4000-650 $cm^{-1}$); the abbreviation "sh" indicates a band appearing as a shoulder.

$^1$H-NMR spectra were recorded at 300.13 MHz using a Bruker DPX-300 model spectrometer. The chemical shifts δ are given in ppm in relation to tetramethyl silane (TMS), coupling constant J are given in Hz. No distinction was made between real and pseudo coupling patterns.

The viscosities were measured on a Rheotec RC30 cone-plate viscometer (ball diameter 50 mm, cone angle 1°, cone tip-plate distance 0.05 mm, shear rate 10-100 $s^{-1}$).

2. Synthesis of Amines of Formula (I)

General Synthesis Procedure for Reductive Alkylation:

An aldehyde and an amine were dissolved in sufficient isopropanol under a nitrogen atmosphere in a round-bottomed flask. The solution was stirred for 30 minutes at room temperature and then hydrogenated at a hydrogen pressure of 80 bar, a temperature of 80° C. and a flow rate of 3 mL/min on a continuous hydrogenation apparatus with Pd/C fixed bed catalyst. To monitor the reaction, IR spectroscopy was used to determine whether the imine band at approximately 1665 $cm^{-1}$ has disappeared. Then the solution was concentrated in vacuo at 80° C.

Example 1

According to the general synthesis procedure for reductive alkylation, 21.45 g 3-hydroxypivalaldehyde and 18.40 g triethylene tetramine (technical grade amine content approximately 25.67 mmol N/g) were reacted. Yield 33.0 g of a clear slightly yellowish oil with a viscosity of 930 mPa·s at 20° C. and an amine content of 12.50 mmol N/g.

FT-IR: 3276 (N—H), 2948, 2868, 2806, 2852, 1732, 1668, 1457, 1361, 1302, 1118, 1054, 906, 771, 702.

Example 2

According to the synthesis procedure for reductive alkylation, 29.87 g 2,2-dimethyl-3-lauroyloxy propanal and 12.0 g polyetherdiamine (Jeffamine® D-230 from Huntsman; amine content 8.29 mmol N/g) were reacted. Yield 38.2 g of a clear pale yellow oil with a viscosity of 260 mPa·s at 20° C. and an amine content of 2.45 mmol N/g.

FT-IR: 2956, 2922, 2871 sh, 2852, 1735 (C=O), 1419, 1393 sh, 1373, 1342w, 1299, 1249, 1236 sh, 1158, 1109, 1012, 991 sh, 928, 864, 765, 722.

$^1$H-NMR (CDCl$_3$, 300 K): ☐3.88 (several s, 4H, OCH$_2$C(CH$_3$)$_2$), 3.6-3.25 (m, approximately 9.7H, OCH$_2$CH(CH$_3$)O and OCH$_2$CH(CH$_3$)NH), 2.75 (m, 2H, OCH$_2$CH(CH$_3$)NH), 2.49-2.35 (several s, 4H, NHCH$_2$C(CH$_3$)$_2$CH$_2$O), 2.31 (t, J=7.5, 4 H, OC(O)CH$_2$), 1.61 (m, 4H, OC(O)CH$_2$CH$_2$), 1.26 (m, 32H, OC(O)CH$_2$CH$_2$(CH$_2$)$_3$CH$_3$), 1.14 and 0.96 (2×m, approximately 11.7H, OCH$_2$CH(CH$_3$)O and OCH$_2$CH(CH$_3$)NH), 0.91 (s, 12H, C(CH$_3$)$_2$), 0.88 (t, J=6.9, 6 H, OC(O)(CH$_2$)$_{10}$CH$_3$).

Example 3

According to the synthesis procedure for reductive alkylation, 29.87 g 2,2-dimethyl-3-lauroyloxy propanal and 8.30 g of a solution of 70% by weight hexamethylene diamine in water. Yield 31.7 g of a clear colorless oil with a viscosity of 240 mPa·s at 20° C. and an amine content of 2.87 mmol N/g.

FT-IR: 2952, 2921, 2852, 2814, 1734 (C=O), 1465, 1420, 1374, 1283 sh, 1248, 1236, 1165, 1114, 1061, 1007, 927, 743 sh, 722.

$^1$H-NMR (CDCl$_3$, 300 K): ☐3.88 (s, 4H, OCH$_2$C(CH$_3$)$_2$), 2.56 (t, J=7.1, 4 H, NHCH$_2$CH$_2$CH$_2$), 2.41 (s, 4H, NHCH$_2$C(CH$_3$)$_2$), 2.31 (t, J=7.5, 4 H, OC(O)CH$_2$), 1.62 (m, 4H, OC(O)CH$_2$CH$_2$), 1.46 (m, 4H, NHCH$_2$CH$_2$CH$_2$), 1.26 (m, 36H, NHCH$_2$CH$_2$CH$_2$ and OC(O)CH$_2$CH$_2$(CH$_2$)$_8$CH$_3$), 1.0 (br s, 2H, NH), 0.92 (s, 12H, C(CH$_3$)$_2$), 0.88 (t, J=6.7, 6 H, OC(O)(CH$_2$)$_{10}$CH$_3$).

Example 4

According to the synthesis procedure for reductive alkylation, 29.87 g 2,2-dimethyl-3-lauroyloxy propanal and 8.52 g 1-amino-3-amino methyl-3,5,5-trimethylcyclohexane (=isophorone diamine). Yield 34.30 g of a clear colorless oil with a viscosity of 450 mPa·s at 20° C. and an amine content of 2.67 mmol N/g.

FT-IR: 2950, 2921, 2871, 2852, 1734 (C=O), 1465, 1419, 1375, 1366 sh, 1350 sh, 1282 sh, 1248, 1235, 1164, 1111, 1006, 987, 932, 895, 865, 736 sh, 721.

$^1$H-NMR (CDCl$_3$, 300 K): □3.89-3.88 (3×s, 4H, OCH$_2$C(CH$_3$)$_2$), 2.63 (m, 1H, NHCH$^{Cy}$), 2.45 (m, 2H, NHCH$_2$C$^{Cy}$), 2.39 and 2.24 (2×s, 2×2 H, NHCH$_2$C(CH$_3$)$_2$), 2.31 (2×t, J=7.5, 4 H, OC(O)CH$_2$), 1.62 (m, 4H, OC(O)CH$_2$CH$_2$), 1.26 (m, 40H, CH$_2^{Cy}$ and OC(O)CH$_2$CH$_2$(CH$_2$)$_8$CH$_3$ and NH), 1.01 (2×s, 3H, C$^{Cy}$CH$_3$), 0.92 (2×s, 18H, C(CH$_3$)$_2$), 0.88 J=6.9, 6 H, OC(O)(CH$_2$)$_{10}$CH$_3$).

Example 5

In a round-bottom flask 11.52 g freshly distilled 2,2-dimethyl-3-methylaminopropanal was placed under a nitrogen atmosphere and then 6.81 g 1,3-bis-(amino methyl)benzene (=meta-xylylene diamine) was added slowly while stirring for 30 minutes at room temperature. The reaction mixture was then combined with 100 mL isopropanol and 10.00 g isopropenyl acetate while stirring for 3 hours at 50° C. and finally hydrogenated and concentrated under the conditions specified in the general synthesis procedure for reductive alkylation. Yield 16.8 g of a clear light orange oil with a viscosity of 9500 mPa·s at 20° C. and an amine content of 5.6 mmol N/g.

FT-IR: 3304 (N—H), 2955, 2868, 2805, 2852, 1658, 1607, 1559, 1443, 1367, 1299, 1220, 1156, 1108, 1033, 953, 909, 788, 748, 701, 682.

Example 6

According to the general synthesis procedure for reductive alkylation, 32.50 g 2,2-dimethyl-3-phenyl propanal and 18.40 g triethylene tetramine (technical grade, amine content approximately 25.67 mmol N/g) were reacted. Yield 45.5 g of a clear yellowish oil with a viscosity of 640 mPa·s at 20° C. and an amine content of 9.35 mmol N/g.

FT-IR: 3302 (N—H), 2946, 2812, 1943, 1733, 1600, 1558, 1493, 1452, 1386, 1362, 1300, 1120, 1072, 1030, 900, 775, 727, 701.

Comparative Example 7

According to the general synthesis procedure for reductive alkylation, 15.14 g isobutyraldehyde and 24.00 g polyether diamine (Jeffamine® D-230 from Huntsman) were reacted. Yield 33.40 g of a clear colorless oil with a viscosity of 170 mPa·s at 20° C. and an amine content of 5.5 mmol N/g.

Comparative Example 8

According to the general synthesis procedure for reductive alkylation, 20.18 g 2-methylpentanal and 24.00 g polyether diamine (Jeffamine® D-230 from Huntsman) were reacted. Yield 39.00 g of clear colorless oil with a viscosity of 160 mPa·s at 20° C. and an amine content of 4.7 mmol N/g.

3. Synthesis of Adducts Having Isocyanate Groups

Substances Used

| | |
|---|---|
| Vestanat® IPDI (Degussa) | Isophorone diisocyanate |
| Jeffamine® SD-231 (Huntsman) | N,N'-Diisopropyl polypropylene glycol diamine, average molecular weight approximately 316 g/mol, amine content approximately 5.80 mmol N/g |
| Jeffamine® SD-2001 (Huntsman) | N,N'-Diisopropyl polypropylene glycol diamine, average molecular weight approximately 2050 g/mol, amine content approximately 0.97 mmol N/g |

Examples 9 and 10 and Comparative Example 11

For each example the amount (in parts by weight) of Vestanat® IPDI listed in Table 1 was added first and then at room temperature under a nitrogen atmosphere while stirring well for three hours the quantities (in parts by weight) of the corresponding amines listed in Table 1 were added by drops. Next the free isocyanate group content of the resulting adducts was determine by titration and the viscosity was also determined.

TABLE 1

Composition and properties of examples 9 and 10 and comparative example 11.

| | Example | | |
|---|---|---|---|
| | 9 | 10 | 11 (comparison) |
| Vestanat® IPDI | 50.00 | 50.00 | 50.00 |
| Amine of example 4 | 37.72 | — | — |
| Amine of example 2 | — | 41.12 | — |
| Jeffamine® SD-231 | — | — | 14.09 |
| Jeffamine® SD-2001 | — | — | 27.15 |
| NCO/NH ratio* | 1:0.24 | 1:0.23 | 1:0.25 |
| NCO content (wt %) | 16.5 | 15.9 | 15.5 |
| Viscosity at 20° C. (mPa · S) | 310 | 1490 | 5200 |

*Ratio of the equivalents of the isocyanate groups used and the secondary amino groups Table 1 shows that the adducts of examples 9 and 10 which contain isocyanate groups and which are adducts AD2—synthesized with a definite excess of polyisocyanate—have a comparatively low viscosity. The adduct of comparative example 11 which also contains isocyanate groups and has a similar structure had a much higher viscosity. This circumstance may be attributable to the excellent diluting properties of the imines of examples 2 and 4 which were used to synthesize the adducts of examples 9 and 10 and which are amines of formula (I b).

4. Synthesis of Compositions Containing Isocyanate Groups

Substances Used

| | |
|---|---|
| Suprasec® 2054 (Huntsman) | Quasi-prepolymer of MDI base with a functionality 2, 15.0% NCO, viscosity (20° C.) 750 mPa · s |
| Jeffamine® D-2000 (Huntsman) (D-2000) | Polypropylene glycol diamine, average molecular weight approximately 2000 g/mol, amine content approximately 0.98 mmol N/g |

-continued

| | |
|---|---|
| Jeffamine ® T-5000 (Huntsman) (T-5000) | Polypropylene glycol triamine, average molecular weight approximately 5000 g/mol, amine content approximately 0.53 mmol N/g |
| Desmophen ® NH 1220 (Bayer) (NH 1220) | Adduct of 1,5-diamino-2-methylpentane and maleic acid diethyl ester in a molar rate of 1:2, amine content approximately 4.35 mmol N/g |
| Desmophen ® NH 1420 (Bayer) (NH 1420) | Adduct of bis-(4-aminocyclohexyl)meane and maleic acid diethyl ester with molecular weight 1:2, amine content approx.. 3.60 mmol N/g |
| Ruetasolv ® DI (Rütgers) (Ruetasolv) | Diisopropyl naphthalene |

Examples 12 to 17 and Comparative Examples 18 and 19

For each example the ingredients listed in Table 2 were mixed in the amounts indicated (in parts by weight) for 15 seconds using a centrifugal mixer (SpeedMixer™ DAC 150, FlackTek Inc.). The time until gelation of the mixture (in short: gel time) was determined for the combined compositions by measuring the viscosity of the combined compositions at regular intervals of time at 20° C. and then defining the gel time as the period of time immediately mixing until exceeding a viscosity of 100 Pa·s.

Polymer P1:

100.0 g polyoxy propylene diol (Desmophen® 2062 BD, Bayer, OH number 56.1 mg KOH/g) and 105.7 g 4,4'-methylenediphenyldiisocyanate (MDT; Desmodur® 44 MC L, Bayer) were reacted at 80° C. to form an NCO-terminated polyurethane polymer containing free isocyanate groups in the amount of 15.0% by weight and having a viscosity of 2300 mPa·s at 20° C.

Polymer P2:

500.0 g polyoxy propylene diol (Acclaim® (Acclaim® 4200 N, Bayer; OH number 28.1 mg KOH/g), 2000.0 g polyoxy propylene polyoxy ethylene triol (Caradol® MD34-02, Shell; OH number 35.0 mg KOH/g) and 245.0 g toluoylene diisocyanate (TDI; Desmodur® T 80 P, Bayer) were reacted at 80° C. to yield an NCO-terminated polyurethane polymer with a free isocyanate group content of 1.88% by weight.

TABLE 2

Composition and gel time of Examples 12 to 17 and Comparative Examples 18 and 19.

| | Example | | | | | | | |
|---|---|---|---|---|---|---|---|---|
| | 12 | 13 | 14 | 15 | 16 | 17 | 18 (comp) | 19 (comp) |
| Polymer P1 | 6.62 | 7.31 | — | — | — | — | 8.61 | 7.89 |
| Polymer P2 | — | — | 9.23 | 12.95 | 13.225 | 13.13 | — | — |
| Ruetasolv | — | — | 5.00 | — | — | — | — | — |
| Example 2* | 8.38 | — | — | 2.05 | — | — | — | — |
| Example 3* | — | 7.69 | — | — | 1.75 | — | — | — |
| Example 4* | — | — | — | — | — | 1.87 | — | — |
| Example 5* | — | — | 0.78 | — | — | — | — | — |
| NH 1220 | — | — | — | — | — | — | 6.39 | — |
| NH 1420 | — | — | — | — | — | — | — | 7.11 |
| Gel time | 4 min | 100 s | 22 min | 13 s | <10 s | 100 s | 12 s | 2 min |

*Amine of the stated example.
"Comp." stands for comparative.

Table 2 shows that Examples 12 and 13 according to the invention with the quasi-prepolymer based on 4,4'-MDI (polymer P1) have comparative high gel times. Examples 14 to 17 according to the invention show that manageable gel times were achieved even with a polyurethane polymer based on TDI (polymer P2).

Examples 20 to 22 and Comparative Examples 23 and 24

For each example the ingredients listed in Table 3 were mixed in the stated amounts (in parts by weight) using a centrifugal mixer (SpeedMixer™ DAC 150, FlackTek Inc.). A film was cast in a layer thickness of approximately 2 mm using each combined composition and the films were then stored for 10 days in a standard climate (23±1° C. and 50±5% relative atmospheric humidity) for curing. The appearance of the films cured in this way was evaluated. A film was classified as "free of defects" if it was clear and free of bubbles and had a non-tacky surface. "Fine bubbles" was used to refer to an otherwise defect-free film that contained just a few fine bubbles. "Cloudy" was used to describe an opaque but otherwise defect-free film. In addition, the mechanical properties of the films cured in this way were tested by exposing the films each to dumbbells with a length 75 mm with a web length of 30 mm and a web width of 4 mm and were tested according to DIN EN 53504 at a pulling rate of 200 mm/min for tensile strength (breaking force), elongation at break and E modulus (at 0.5-5.0% elongation) and also the Shore hardness (AJD) was determined in accordance with DIN 53505.

TABLE 3

Composition and properties of Examples 20 to 22 and comparative examples 23 and 24. "Comp." stands for Comparative.

| | Example | | | | |
|---|---|---|---|---|---|
| | 20 | 21 | 22 | 23 (comp) | 24 (comp) |
| Suprasec ® 2054 | — | 100.0 | 100.0 | 100.0 | 100.0 |
| Polymer P1 | 100.0 | — | — | — | — |
| Jeffamine ® D-2000 | 47.0 | 47.0 | 47.0 | 47.0 | 47.0 |
| Jeffamine ® T-5000 | 10.0 | 10.0 | 10.0 | 10.0 | 10.0 |
| Amine of example 3 | 90.4 | 90.4 | — | — | — |
| Amine of example 4 | — | — | 97.9 | — | — |

TABLE 3-continued

Composition and properties of Examples 20 to 22 and comparative examples 23 and 24. "Comp." stands for Comparative.

| | Example | | | | |
|---|---|---|---|---|---|
| | 20 | 21 | 22 | 23 (comp) | 24 (comp) |
| NH 1220 | — | — | — | 64.0 | — |
| NH 1420 | — | — | — | — | 77.6 |
| Tensile strength (MPa) | 0.8 | 1.1 | 3.8 | 8.6 | 16.8 |
| Elongation at break (%) | 1130 | 730 | 760 | 580 | 330 |
| Elastic modulus (MPa) | 1.9 | 0.9 | 4.6 | 53.9 | 199.7 |
| Shore hardness | 41 A | 45 A | 61 A | 34 D | 53 D |
| Appearance | fine bubbles | fine bubbles | defect free | cloudy | fine bubbles |

It can be seen from Table 3 that Examples 20 to 22 according to the invention were cured to form attractive films with a high ductility and flexibility.

5. Synthesis of Epoxy Resin Compositions

Substances Used:

| | |
|---|---|
| Araldite ® GY 250 (Huntsman) | Bisphenol A-diglycidyl ether, EEW approximately 187.5 g/Eq |
| Araldite ® DY-E (Huntsman) | Monoglycidyl ether of a $C_{12}$ to $C_{14}$ alcohol, EEW approximately 290 g/Eq |
| Ancamine ® K 54 (Air Products) | 2,4,6-Tris-(dimethylamino methyl)phenol |

Examples 25 to 27 and Comparative Examples 28 and 29

For each example, the ingredients listed in Table 4 were mixed in the amounts indicated (in parts by weight) using a centrifugal mixer (SpeedMixer™ DAC 150, FlackTek Inc.). Using the combined compositions, the viscosity was determined 10 minutes after mixing at 20° C., if indicated. In addition, a film with a layer thickness of 500 μm was applied to a sheet of glass which was then stored at 23° C. and 50% relative atmospheric humidity (=standard climate, abbreviated below "STP") and cured. After 4 weeks the appearance of the films was evaluated. A film was classified as "defect-free" if it was clear and had a hard shiny non-tacky surface without any structure. The term "structure" here refers to any form of patterning or lines on the surface. The term "matte" was used to denote a film that was clear and had a hard non-tacky surface without structure but also without any gloss. "Cloudy" was used to refer to an opaque but non-tacky film. In addition, the Koenig hardness (pendulum hardness according to Koenig) was measured according to DIN EN ISO 1522) of the films was determined after 7 days (Koenig hardness (7 d)) and after 4 weeks (Koenig hardness (4w)).

The results are given in Table 4.

TABLE 4

Composition and properties of examples 25 to 27 and comparative Examples 28 and 29. "Comp." stands for comparative.

| | Example | | | | |
|---|---|---|---|---|---|
| | 25 | 26 | 27 | 28 (comp) | 29 (comp) |
| Araldite ® GY-250 | 167.2 | 167.2 | 167.2 | 167.2 | 167.2 |
| Araldite ® DY-E | 31.8 | 31.8 | 31.8 | 31.8 | 31.8 |
| Isophorone diamine | — | 27.9 | — | 8.3 | 28.3 |
| Example 1* | 79.6 | — | — | — | — |
| Example 5* | — | 73.3 | — | — | — |
| Example 6* | — | — | 109.7 | — | — |
| Comparative example 7* | — | — | — | 58.7 | — |
| Comparative example 8* | — | — | — | — | 68.0 |
| Ancamine ® K 54 | 5.6 | 6.0 | 6.2 | 5.7 | 5.9 |
| Viscosity (10 s) (Pa·s) | 1.2 | 1.8 | 1.1 | 0.34 | 0.31 |
| Koenig hardness (s) (7 d) | 178 | 139 | 88 | 99 | 62 |
| (4 w) | 181 | 167 | 112 | 134 | 78 |
| Appearance | defect free | matte | defect free | cloudy | cloudy |

*Amine of the example indicated

Table 4 shows that the amines of Examples 1, 5 and 6 have an excellent compatibility with the respective epoxy resin compositions of Examples 25 to 27, while the amines of Comparative Examples 7 and 8 yielded cloudy films in curing of Comparative Examples 28 and 29, which is an indication of an inadequate incompatibility of the amine with the epoxy resin.

The invention claimed is:
1. An amine of formula (I)

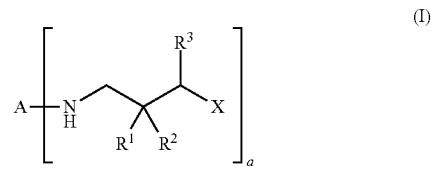

in which
A stands for a radical of an amine after removal of a primary aliphatic amino group(s);
a stands for an integer from 1 to 6 with the provision that in the case when a=1, the radical A has at least one reactive group selected from the group consisting of primary amino groups, mercapto groups, and silane groups;
$R^1$ and $R^2$ either
independently of one another each stand for a monovalent hydrocarbon radical with 1 to 12 carbon atoms,
or together they stand for a divalent hydrocarbon radical with 4 to 12 carbon atoms, which is part of an optionally substituted carbocyclic ring with 5 to 8 carbon atoms;
$R^3$ stands for a hydrogen atom or an alkyl group or an arylalkyl group or an alkoxycarbonyl group each with 1 to 12 carbon atoms; and
X stands for a radical selected from the group consisting of $X^a$, $X^b$, and $X^c$,
wherein
$X^a$ stands for —$OR^4$ where
$R^4$ stands for a hydrogen or a hydrocarbon radical with 1 to 20 carbon atoms, optionally having at least one heteroatom, $X^b$ stands for

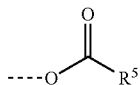

wherein $R^5$ stands for a hydrogen or a hydrocarbon radical with 1 to 20 carbon atoms, which optionally has at least one heteroatom; and $X^c$ stands for

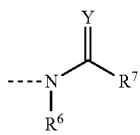

wherein

Y stands for O or S and $R^6$ and $R^7$ either together stand for a divalent radical having 2 to 10 carbon atoms, optionally having oxygen or sulfur atoms, the divalent radical being part of optionally substituted five-, six- or seven-membered ring, or $R^6$ stands for an alkyl, cycloalkyl, arylalkyl or acyl radical with 1 to 10 carbon atoms and $R^7$ stands for a hydrogen or a monovalent radical with 1 to 20 carbon atoms, selected from the group consisting of an alkyl radical, cycloalkyl radical, arylalkyl radical, aryl radical, —$OR^8$, —$SR^8$ and —$NR^8R^9$, where $R^8$ and $R^9$ either each stand for a hydrocarbon radical or together stand for an alkylene radical which is part of five-, six- or seven-membered ring.

2. The amine of formula (I) according to claim 1, wherein $R^1$ and $R^2$ each stand for a methyl radical and/or $R^3$ stands for a hydrogen atom.

3. The amine of formula (I) according to claim 1, wherein X stands for $X^a$; and $R^4$ stands for a hydrogen atom or for a hydrocarbon radical with 1 to 12 carbon atoms, optionally containing an ether oxygen.

4. The amine of formula (I) according to claim 1, wherein X stands for $X^b$; and $R^5$ stands for a hydrogen atom, or a linear or branched alkyl radical with 1 to 11 carbon atoms, optionally with cyclic fractions and optionally with at least one heteroatom, or a mono- or polyunsaturated linear or branched hydrocarbon radical with 5 to 11 carbon atoms, or an optionally substituted aromatic or heteroaromatic six-membered ring.

5. The amine of formula (I) according to claim 1, wherein X stands for $X^c$.

6. A method for synthesis of an amine of formula (I) according to claim 1, wherein at least one amine PA of formula (II) is reductively alkylated with at least one aldehyde ALD of formula (III)

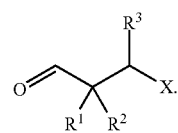

7. The method of synthesis of an amine of formula (I) according to claim 6, wherein the process is carried out in such a way that at least one amine PA of formula (II) is condensed with at least one aldehyde ALD of formula (III) to form an aldimine which is then hydrogenated.

8. The method according to claim 6, wherein the amine PA of formula (II) is selected from the group consisting of 1,5-diamino-2-methylpentane (MPMD), 2-butyl-2-ethyl-1,5-pentane diamine (C11-neodiamine), 1,6-hexane diamine, 2,5-dimethyl-1,6-hexane diamine, 2,2,4- and 2,4,4-trimethylhexamethylene diamine (TMD), 1,12-dodecane diamine, 1,4-diaminocyclohexane, bis-(4-aminocyclohexyl)methane ($H_{12}$-MDA), bis-(4-amino-3-methylcyclohexyl)methane, 1-amino-3-amino methyl 3,5,5-trimethylcyclohexane (=isophorone diamine or IPDA), 1,3-bis-(amino methyl)cyclohexane, 2,5(2,6)-bis-(amino methyl)bicyclo[2.2.1]heptane (NBDA), 3(4),8(9)-bis-(amino methyl)tricyclo[5.2.1.0$^{2,6}$] decane, 1,3-xylylene diamine, bis-hexamethylene triamine (BHMT), diethylene triamine (DETA), triethylene tetramine (TETA), tetraethylene pentamine (TEPA), pentaethylenehexamine (PEHA), polyethylene polyamine with 5 to 7 ethyleneamine units (so-called higher ethylene polyamine, HEPA), dipropylene triamine (DPTA), N-(2-amino ethyl)-1,3-propane diamine (N3 amine), N,N-bis(3-aminopropyl)-ethylene diamine (N4 amine) and polyoxy alkylene diamine and polyoxy alkylene triamine.

9. The method according to claim 6, wherein the aldehyde ALD of formula (III) is selected from the group consisting of 2,2-dimethyl-3-hydroxy propanal, 2,2-dimethyl-3-methoxy propanal, 2,2-dimethyl-3-ethoxy propanal, 2,2-dimethyl-3-propoxy propanal and propoxy isomers thereof, 3-butoxy-2,2-dimethyl propanal and butoxy isomers thereof, 2,2-dimethyl 3-pentoxy propanal and thereof, 2,2-dimethyl-3-hexoxy propanal and hexoxy isomers thereof, 3 cyclohexyloxy-2,2-dimethyl propanal, 2,2-dimethyl 3-(2-ethylhexyloxyl) propanal, 2,2-dimethyl-3-lauroxy propanal, 2,2-dimethyl 3-formyloxy propanal, 3-acetoxy-2,2-dimethyl propanal, 2,2-dimethyl 3-propionyloxy propanal, 3-butyroxy-2,2-dimethyl propanal, 2,2-dimethyl 3-isobutyroxy propanal, 2,2-dimethyl-3-valeroyloxy propanal, 2,2-dimethyl 3-hexanoyloxy propanal, 2,2-dimethyl-3-(2-ethylhexanoyloxy) propanal, 2,2-dimethyl-3-octanoyloxy propanal, 3-decanoyloxy-2,2-dimethyl propanal, 2,2-dimethyl-3-lauroyloxy propanal, 3-cyclohexanoyloxy-2,2-dimethyl propanal, N-(2,2-dimethyl-3-oxopropyl)-N-methylformamide, N-(2,2-dimethyl-3-oxopropyl)-N-methylacetamide, N-(2,2-dimethyl 3-oxopropyl)-N-butylacetamide, N-(2,2-dimethyl-3-oxopropyl)-N-(2-ethylhexyl)acetamide, N-(2,2-dimethyl-3-oxopropyl)-N-methylbutyramide, N-(2,2-dimethyl-3-oxopropyl)N-methyl-(2-ethylcaproamide), O-ethyl-N-(2,2-dimethyl-3-oxopropyl)-N-methylcarbamate, N-(2,2-dimethyl-3-oxopropyl)pyrrolidin-2-one, N-(2,2-dimethyl-3-oxopropyl)piperidin-2-one, N-(2,2-dimethyl-3-oxopropyl)azepan-2-one, N-(2,2-dimethyl 3-oxopropyl)oxazolidin-2-one, N-(2,2-dimethyl-3-oxopropyl)thiazolidin-2-one, and N-(2,2-dimethyl-3-oxopropyl)pyrrolidine-2,5-dione.

10. An adduct AD obtained from the reaction of at least one amine of formula (I) according to claim 1 with at least one compound VB having at least one reactive group RG, where the reactive group RG is selected from the group consisting of isocyanate, isothiocyanate, cyclocarbonate, epoxide, episulfide, aziridine, acryl, methacryl, 1-ethynylcarbonyl, 1-propinylcarbonyl, maleimide, citraconimide, vinyl, isopropenyl and allyl groups.

11. The adduct AD according to claim 10, wherein it is an adduct AD1 having at least two amino groups of formula (XII)

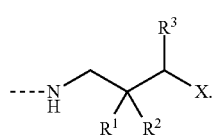

12. The adduct AD according to claim 10, wherein it is an adduct AD2 having at least two isocyanate groups, using a polyisocyanate as compound VB.

13. An article of manufacture including an adduct AD according to claim 10, the article being selected from the group comprising fiber composite materials (composites), casting compounds, sealants, adhesives, coatings, paints enamels, fields, primers, foundations, foams, molded blocks, elastomers, fibers, films and membranes.

14. An epoxy resin composition Z2 containing
a) at least one epoxy resin and
b) at least one amine of formula (I) according to claim 1.

15. An article of manufacture including the amine of formula (I) according to claim 1, the article being selected from the group comprising fiber composite materials (composites), casting compounds, sealants, adhesives, coatings, paints enamels, fields, primers, foundations, foams, molded blocks, elastomers, fibers, films and membranes.

16. The amine of formula (I) according to claim 1, wherein a stands for 1.

17. The amine of formula (I) according to claim 1, wherein a stands for 2.

18. A composition Z1 containing isocyanate groups and having
a) at least one polyisocyanate and
b) at least one curing agent compound HV which has at least two reactive groups selected from the group consisting of primary amino groups, and mercapto groups;
with the provision that the curing agent compound HV is a compound selected from the group consisting of the amines of formula (I)

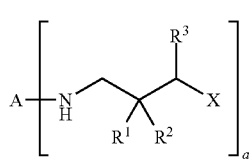

in which
A stands for the radical of an amine after removal of a primary aliphatic amino group(s);

a stands for an integer from 1 to 6 with the provision that in the case when a=1, the radical A has at least one reactive group selected from the group consisting of primary amino groups, mercapto groups and silane groups;

$R^1$ and $R^2$ either
independently of one another each stand for a monovalent hydrocarbon radical with 1 to 12 carbon atoms,
or together they stand for a divalent hydrocarbon radical with 4 to 12 carbon atoms, which is part of an optionally substituted carbocyclic ring with 5 to 8 carbon atoms;

$R^3$ stands for a hydrogen atom or an alkyl group or an arylalkyl group or an alkoxycarbonyl group each with 1 to 12 carbon atoms; and X stands for a radical selected from the group consisting of $X^a$, $X^b$, and $X^c$, wherein $X^a$ stands for —$OR^4$ where
$R^4$ stands for a hydrogen or a hydrocarbon radical with 1 to 20 carbon atoms, optionally having at least one heteroatom;

$X^b$ stands for

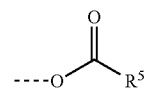

wherein
$R^5$ stands for a hydrogen or a hydrocarbon radical with 1 to 20 carbon atoms, which optionally has at least one heteroatom; and $X^c$ stands for

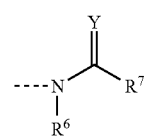

wherein
Y stands for O or S and
$R^6$ and $R^7$ either
together stand for a divalent radical having 2 to 10 carbon atoms, optionally having oxygen or sulfur atoms, this radical being part of optionally substituted five-, six- or seven-membered ring,
or
$R^6$ stands for an alkyl, cycloalkyl, arylalkyl or acyl radical with 1 to 10 carbon atoms and
$R^7$ stands for a hydrogen or a monovalent radical with 1 to 20 carbon atoms, selected from the group consisting of an alkyl radical, cycloalkyl radical, arylalkyl radical, aryl radical, —$OR^8$, —$SR^8$ and —$NR^8R^9$,
where $R^8$ and $R^9$ either each stand for a hydrocarbon radical or together stand for an alkylene radical which is part of five-, six- or seven-membered ring.

19. An amine of formula (I)

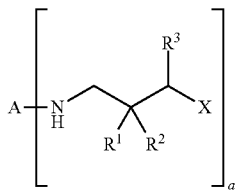

in which

A stands for a radical of an amine after removal of a primary aliphatic amino group(s);

a stands for an integer of 2 or 3;

$R^1$ and $R^2$ either independently of one another each stand for a monovalent hydrocarbon radical with 1 to 12 carbon atoms, or together they stand for a divalent hydrocarbon radical with 4 to 12 carbon atoms, which is part of an optionally substituted carbocyclic ring with 5 to 8 carbon atoms;

$R^3$ stands for a hydrogen atom or an alkyl group or an arylalkyl group or an alkoxycarbonyl group each with 1 to 12 carbon atoms; and X stands for a radical selected from the group consisting of $X^a$, $X^b$, and $X^c$, wherein $X^a$ stands for —$OR^4$ where $R^4$ stands for a hydrogen or a hydrocarbon radical with 1 to 20 carbon atoms, optionally having at least one heteroatom, $X^b$ stands for

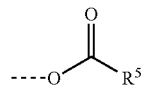

wherein $R^5$ stands for a hydrogen or a hydrocarbon radical with 1 to 20 carbon atoms, which optionally has at least one heteroatom; and $X^c$ stands for

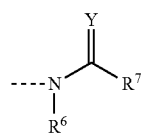

wherein

Y stands for O or S and $R^6$ and $R^7$ either together stand for a divalent radical having 2 to 10 carbon atoms, optionally having oxygen or sulfur atoms, the divalent radical being part of optionally substituted five-, six- or seven-membered ring, or $R^6$ stands for an alkyl, cycloalkyl, arylalkyl or acyl radical with 1 to 10 carbon atoms and $R^7$ stands for a hydrogen or a monovalent radical with 1 to 20 carbon atoms, selected from the group consisting of an alkyl radical, cycloalkyl radical, arylalkyl radical, aryl radical, —$OR^8$, —$SR^8$ and —$NR^8R^9$, where $R^8$ and $R^9$ either each stand for a hydrocarbon radical or together stand for an alkylene radical which is part of five-, six- or seven-membered ring.

\* \* \* \* \*